US010087142B2

(12) United States Patent
Pettersson et al.

(10) Patent No.: US 10,087,142 B2
(45) Date of Patent: Oct. 2, 2018

(54) AZETIDINE DERIVATIVES USEFUL AS MODULATORS OF CORTICAL CATHECOLAMINERGIC NEUROTRANSMISSION

(71) Applicant: Integrative Research Laboratories Sweden AB, Göteborg (SE)

(72) Inventors: Fredrik Pettersson, Göteborg (SE); Clas Sonesson, Billdal (SE)

(73) Assignee: INTEGRATIVE RESEARCH LABORATORIES, Göteborg (SE)

( * ) Notice: Subject to any disclaimer, the term of this patent is extended or adjusted under 35 U.S.C. 154(b) by 0 days.

(21) Appl. No.: 15/574,796

(22) PCT Filed: May 20, 2016

(86) PCT No.: PCT/EP2016/061479
§ 371 (c)(1),
(2) Date: Nov. 16, 2017

(87) PCT Pub. No.: WO2016/185032
PCT Pub. Date: Nov. 24, 2016

(65) Prior Publication Data
US 2018/0141903 A1    May 24, 2018

(30) Foreign Application Priority Data

May 20, 2015   (EP) ..................................... 15168373
Apr. 11, 2016  (SE) ..................................... 1650485

(51) Int. Cl.
C07D 205/04      (2006.01)
A61P 25/28       (2006.01)
A61P 25/18       (2006.01)
A61P 25/22       (2006.01)
A61P 25/14       (2006.01)

(52) U.S. Cl.
CPC ............ *C07D 205/04* (2013.01); *A61P 25/14* (2018.01); *A61P 25/18* (2018.01); *A61P 25/22* (2018.01); *A61P 25/28* (2018.01)

(58) Field of Classification Search
CPC ........ C07D 205/04; A61P 25/14; A61P 25/28; A61P 25/22; A61P 25/18
USPC .................................................. 514/210.01
See application file for complete search history.

(56) References Cited

U.S. PATENT DOCUMENTS

| 2011/0257148 | A1* | 10/2011 | Sonesson | ............ | C07D 205/04 |
| | | | | | 514/210.01 |
| 2011/0257241 | A1* | 10/2011 | Sonesson | ............ | C07D 207/12 |
| | | | | | 514/424 |
| 2011/0281835 | A1* | 11/2011 | Sonesson | ............ | C07D 205/04 |
| | | | | | 514/210.01 |
| 2014/0171402 | A1* | 6/2014  | Hahn     | .................... | C07D 205/04 |
| | | | | | 514/210.17 |

FOREIGN PATENT DOCUMENTS

| EP | 2754653 A2 | 7/2014 |
| WO | WO 2004/113297 A2 | 12/2004 |
| WO | WO 2008/148801 A2 | 12/2008 |
| WO | WO 2010/058017 A1 | 5/2010 |

OTHER PUBLICATIONS

Han; J. Med. Chem. 2012, 55, 8188-8192. (Year: 2012).*
Chen; Expert Opinion on Investigational Drugs, 2007, 16, 1365-1377. (Year: 2007).*
Arnsten, A.F.T., Catecholamine Influences on Dorsolateral Prefrontal Cortical Networks. Biol Psychiatry. 2011; 69(12): e89-99.
Berge, S.M. et al., Pharmaceutical Salts. J Pharm Sci. 1977; 66(1): 1-19.
Bramham, C.R. et al., The Arc of Synaptic Memory. Exp Brain Res. 2010; 200(2): 125-40.
Chomczynski, P. and Sacchi, N., Single-Step Method of RNA Isolation by Acid Guanidinium Thiocyanare-Phenol-Chloroform Extraction. Anal Biochem. 1987; 162(1): 156-9.
Harrison, P.J. et al., Schizophrenia Genes, Gene Expression, and Neuropathology: on the Matter of Their Convergence. Mol Psychiatry. 2005; 10(1): 40-68.
Kawashima, T. et al., Synaptic Activity-Responsive Element in the Arc/Arg3.1 Promoter Essential for Synapse-to-Nucleus Signaling in Activated Neurons. Proc Nat Acad Sci. 2009; 106(1): 316-21.
Link, W. et al., Somatodendritic Expression of an Immediate Early Gene is Regulated by Synaptic Activity. Proc Nat Acad Sci U.S.A. 1995; 92(12): 5734-8.
Lyford, G.L. et al., Arc, A Growth Factor and Activity-Regulated Gene, Encodes a Novel Cytoskeleton-Associated Protein That is Enriched in Neuronal Dendrites. Neuron. 1995; 14(2): 433-45.
Moghaddam, B. and Bunney, B.S., Ionic Composition of Microdialysis Perfusing Solution Alters the Pharmacological Responsiveness and Basal Outflow of Striatal Dopamine. J Neurochem. 1989; 53(2): 652-4.
Paulekuhn, G.S. et al., Trends in Active Pharmaceutical Ingredient Salt Selection Based on Analysis of the Orange Book Database. J Med Chem. 2007; 50: 6665-72.
Paxinos and Watson, The Rat Brain in Stereotaxic Coordinates. 2nd Ed. New York, Academic Press. 1986; Fig 8 and Fig 14.
Rautio et al., Prodrugs: Design and Clinical Applications. Nat Rev Drug Discov. 2008; 7(3): 255-70.
Renwick, A.B. et al., Metabolism of 2,5-bis(trifluoromethyl)-7-benzyloxy-4-trifluoromethylcoumarin by Human Hepatic CYP Isoforms: Evidence for Selectivity Towards CYP3A4. Xenobiotica. 2001; 31(4): 187-204.
Steward, O. and Worley, P.F., Selective Targeting of Newly Synthesized Arc mRNA to Active Synapses Requires NMDA Receptor Activation. Neuron. 2001; 30(1): 227-40.

(Continued)

*Primary Examiner* — Daniel R Carcanague
(74) *Attorney, Agent, or Firm* — Ballard Spahr LLP

(57) ABSTRACT

The present disclosure relates to certain novel compounds of Formula (I) and to their utility in modulation of levels of monoamines, dopamine, norepinephrine and serotonin, in cerebral cortical areas of the mammalian brain, and more specifically for the treatment of central nervous system disorders.

26 Claims, No Drawings
Specification includes a Sequence Listing.

(56) References Cited

OTHER PUBLICATIONS

International Search Report and Written Opinion dated Jul. 25, 2016 by the International Searching Authority for Patent Application No. PCT/EP2016/061479, which was filed on May 20, 2016 and published as WO 2016/185032 dated Nov. 24, 2016 (Inventor—Pettersson et al.; Applicant—Valea AB) (9 pages).

Abi-Dargham, A. et al., Mechanisms of Action of Second Generation Antipsychotic Drugs in Schizophrenia: Insights From Brain Imaging Studies. Eur Psych. 2005; 20: 15-27.

Crespi, C.L. and Stresser, D.M., Fluorometric Screening for Metabolism-Based Drug-Drug Interactions. J Pharm Tox Meth. 2000; 44: 325-31.

Hamon, M. and Blier, P., Monoamine Neurocircuitry in Depression and Strategies for New Treatments. Prog Neuropsychopharmacol Biol Psychiatry. 2013; 45: 54-63.

Santiago, M. and Westerink, B.H., Characterization of the in vivo Release of Dopamine as Recorded by Different Types of Intracerebral Microdialysis Probes. Naunyn Schmiedebergs Arch Pharmacol. 1990; 342(4): 407-14.

Trillo, L. et al., Ascending Monoaminergic Systems Alterations in Alzheimer's Disease. Translating Basic Science into Clinical Care. Neurosci Biobehav Rev. 2013; 37(8): 1363-79.

Wang, H. et al., Targeted Pharmacological Treatment for Autism Spectrum Disorders: Fragile X and Rett Syndromes. Front Cell Neurosci. 2015; 9(55): 1-23.

Waters, N. et al., Differential Effects of Dopamine D2 and D3 Receptor Antagonists in Regard to Dopamine Release, in vivo Receptor Displacement and Behaviour. J Neural Transm Gen Sect. 1994; 98(1): 39-55.

\* cited by examiner

SEQUENCE LISTING

<160> NUMBER OF SEQ ID NOS: 30

<210> SEQ ID NO 1
<211> LENGTH: 20
<212> TYPE: DNA
<213> ORGANISM: Artificial Sequence
<220> FEATURE:
<223> OTHER INFORMATION: Activity-regulated gene (Arc) (accession number
      U19866) sense primer

<400> SEQUENCE: 1
ggagttcaag aaggagtttc                                              20

<210> SEQ ID NO 2
<211> LENGTH: 19
<212> TYPE: DNA
<213> ORGANISM: Artificial Sequence
<220> FEATURE:
<223> OTHER INFORMATION: Activity-regulated gene (Arc) (accession number
      U19866) antisense primer

<400> SEQUENCE: 2
ccacatacag tgtctggta                                               19

<210> SEQ ID NO 3
<211> LENGTH: 20
<212> TYPE: DNA
<213> ORGANISM: Artificial Sequence
<220> FEATURE:
<223> OTHER INFORMATION: Activity-regulated gene (Arc) (accession number
      U19866) probe

<400> SEQUENCE: 3
ccgcttacgc cagaggaact                                              20

<210> SEQ ID NO 4
<211> LENGTH: 20
<212> TYPE: DNA
<213> ORGANISM: Artificial Sequence
<220> FEATURE:
<223> OTHER INFORMATION: Hypoxantine phosphoribosyl transferase (HPRT)
      (accession number AF001282) sense primer 01

<400> SEQUENCE: 4
agggatttga atcatgtttg                                              20

<210> SEQ ID NO 5
<211> LENGTH: 19
<212> TYPE: DNA
<213> ORGANISM: Artificial Sequence
<220> FEATURE:
<223> OTHER INFORMATION: Hypoxantine phosphoribosyl transferase (HPRT)
      (accession number AF001282) antisense primer 01

<400> SEQUENCE: 5
ctgctagttc tttactggc                                                  19

<210> SEQ ID NO 6
<211> LENGTH: 23
<212> TYPE: DNA
<213> ORGANISM: Artificial Sequence
<220> FEATURE:
<223> OTHER INFORMATION: Hypoxantine phosphoribosyl transferase (HPRT)
      (accession number AF001282) probe 01

<400> SEQUENCE: 6
tgtagattca acttgccgct gtc                                             23

<210> SEQ ID NO 7
<211> LENGTH: 18
<212> TYPE: DNA
<213> ORGANISM: Artificial Sequence
<220> FEATURE:
<223> OTHER INFORMATION: Cyclophilin A (cyclo) (accession number M19533)
      sense primer 01

<400> SEQUENCE: 7
ctggaccaaa cacaaatg                                                   18

<210> SEQ ID NO 8
<211> LENGTH: 18
<212> TYPE: DNA
<213> ORGANISM: Artificial Sequence
<220> FEATURE:
<223> OTHER INFORMATION: Cyclophilin A (cyclo) (accession number M19533)
      antisense primer 01

<400> SEQUENCE: 8
atgccttctt tcaccttc                                                   18

<210> SEQ ID NO 9
<211> LENGTH: 20
<212> TYPE: DNA
<213> ORGANISM: Artificial Sequence
<220> FEATURE:
<223> OTHER INFORMATION: Cyclophilin A (cyclo) (accession number M19533)
      probe 01

<400> SEQUENCE: 9
ttgccatcca gccactcagt                                                 20

<210> SEQ ID NO 10
<211> LENGTH: 22
<212> TYPE: DNA
<213> ORGANISM: Artificial Sequence
<220> FEATURE:
<223> OTHER INFORMATION: Brain Derived Neurotrophic Factor (bdnf)
      (accession number NM_012513) sense primer

<400> SEQUENCE: 10
aaattacctg gatgccgcaa ac                                              22

<210> SEQ ID NO 11
<211> LENGTH: 22
<212> TYPE: DNA
<213> ORGANISM: Artificial Sequence
<220> FEATURE:
<223> OTHER INFORMATION: Brain Derived Neurotrophic Factor (bdnf)
      (accession number NM_012513) antisense primer

<400> SEQUENCE: 11
tgtgacccac tcgctaatac tg                                              22

<210> SEQ ID NO 12
<211> LENGTH: 23
<212> TYPE: DNA
<213> ORGANISM: Artificial Sequence
<220> FEATURE:
<223> OTHER INFORMATION: Brain Derived Neurotrophic Factor (bdnf)
      (accession number NM_012513) probe

<400> SEQUENCE: 12
cacacacgct cagctcccca cgg                                             23

<210> SEQ ID NO 13
<211> LENGTH: 18
<212> TYPE: DNA
<213> ORGANISM: Artificial Sequence
<220> FEATURE:
<223> OTHER INFORMATION: Rattus norvegicus proto-oncogen (c-fos)
      (accession number DQ089699) sense primer

<400> SEQUENCE: 13
cagagcatcg gcagaagg                                                   18

<210> SEQ ID NO 14
<211> LENGTH: 21
<212> TYPE: DNA
<213> ORGANISM: Artificial Sequence
<220> FEATURE:
<223> OTHER INFORMATION: Rattus norvegicus proto-oncogen (c-fos)
      (accession number DQ089699) antisense primer

<400> SEQUENCE: 14
agttgatctg tctccgcttg g                                               21

<210> SEQ ID NO 15
<211> LENGTH: 26
<212> TYPE: DNA
<213> ORGANISM: Artificial Sequence
<220> FEATURE:
<223> OTHER INFORMATION: Rattus norvegicus proto-oncogen (c-fos)
      (accession number DQ089699) probe

<400> SEQUENCE: 15
tctgtcagct ccctcctccg attccg                                          26

<210> SEQ ID NO 16
<211> LENGTH: 22
<212> TYPE: DNA
<213> ORGANISM: Artificial Sequence
<220> FEATURE:
<223> OTHER INFORMATION: Glutamic acid decarboxylase (GAD 67) (accession
      number 34445) sense primer

<400> SEQUENCE: 16
ctgtttatgg agcgtttgat cc                                              22

```
<210> SEQ ID NO 17
<211> LENGTH: 22
<212> TYPE: DNA
<213> ORGANISM: Artificial Sequence
<220> FEATURE:
<223> OTHER INFORMATION: Glutamic acid decarboxylase (GAD 67) (accession
      number 34445) antisense primer

<400> SEQUENCE: 17
gactgagact gacctttcta tg                                              22

<210> SEQ ID NO 18
<211> LENGTH: 22
<212> TYPE: DNA
<213> ORGANISM: Artificial Sequence
<220> FEATURE:
<223> OTHER INFORMATION: Glutamic acid decarboxylase (GAD 67) (accession
      number 34445) probe

<400> SEQUENCE: 18
gactgaattg gccctttcta tg                                              22

<210> SEQ ID NO 19
<211> LENGTH: 19
<212> TYPE: DNA
<213> ORGANISM: Artificial Sequence
<220> FEATURE:
<223> OTHER INFORMATION: Glutamate dehydrogenase (glud) (accession
      number NM_012570) sense primer

<400> SEQUENCE: 19
agcctctcct tccccatcc                                                  19

<210> SEQ ID NO 20
<211> LENGTH: 20
<212> TYPE: DNA
<213> ORGANISM: Artificial Sequence
<220> FEATURE:
<223> OTHER INFORMATION: Glutamate dehydrogenase (glud) (accession
      number NM_012570) antisense primer

<400> SEQUENCE: 20
cgccttcacc tcatccacac                                                 20

<210> SEQ ID NO 21
<211> LENGTH: 21
<212> TYPE: DNA
<213> ORGANISM: Artificial Sequence
<220> FEATURE:
<223> OTHER INFORMATION: Glutamate dehydrogenase (glud) (accession
      number NM_012570) probe

<400> SEQUENCE: 21
agcacagcca gcaccgcacg c                                               21

<210> SEQ ID NO 22
<211> LENGTH: 19
<212> TYPE: DNA
<213> ORGANISM: Artificial Sequence
<220> FEATURE:
<223> OTHER INFORMATION: Preproenkephalin (penk) (accession number
      NM_017139.1) sense primer

<400> SEQUENCE: 22
catgtgctgc ttgtgctgt                                                  19

<210> SEQ ID NO 23
```

```
<211> LENGTH: 19
<212> TYPE: DNA
<213> ORGANISM: Artificial Sequence
<220> FEATURE:
<223> OTHER INFORMATION: Preproenkephalin (penk) (accession number
      NM_017139.1) antisense primer

<400> SEQUENCE: 23
cagttgggtt cacgggttt                                                  19

<210> SEQ ID NO 24
<211> LENGTH: 24
<212> TYPE: DNA
<213> ORGANISM: Artificial Sequence
<220> FEATURE:
<223> OTHER INFORMATION: Preproenkephalin (penk) (accession number
      NM_017139.1) probe

<400> SEQUENCE: 24
tgccctcgtg gtctggataa ctgc                                            24

<210> SEQ ID NO 25
<211> LENGTH: 21
<212> TYPE: DNA
<213> ORGANISM: Artificial Sequence
<220> FEATURE:
<223> OTHER INFORMATION: Hypoxantine phosphoribosyl transferase (HPRT)
      (accession number AF001282) sense primer 02

<400> SEQUENCE: 25
ggccagactt tgttggattt g                                               21

<210> SEQ ID NO 26
<211> LENGTH: 20
<212> TYPE: DNA
<213> ORGANISM: Artificial Sequence
<220> FEATURE:
<223> OTHER INFORMATION: Hypoxantine phosphoribosyl transferase (HPRT)
      (accession number AF001282) antisense primer 02

<400> SEQUENCE: 26
ccgctgtctt ttaggctttg                                                 20

<210> SEQ ID NO 27
<211> LENGTH: 28
<212> TYPE: DNA
<213> ORGANISM: Artificial Sequence
<220> FEATURE:
<223> OTHER INFORMATION: Hypoxantine phosphoribosyl transferase (HPRT)
      (accession number AF001282) probe 02

<400> SEQUENCE: 27
tttccacttt cgctgatgac acaaacat                                        28

<210> SEQ ID NO 28
<211> LENGTH: 20
<212> TYPE: DNA
<213> ORGANISM: Artificial Sequence
<220> FEATURE:
<223> OTHER INFORMATION: Cyclophilin A (cyclo) (accession number M19533)
      sense primer 02

<400> SEQUENCE: 28
gtctcttttc gccgcttgct                                                 20

<210> SEQ ID NO 29
<211> LENGTH: 25
```

```
<212> TYPE: DNA
<213> ORGANISM: Artificial Sequence
<220> FEATURE:
<223> OTHER INFORMATION: Cyclophilin A (cyclo) (accession number M19533)
      antisense primer 02

<400> SEQUENCE: 29
tctgctgtct ttggaacttt gtctg                                        25

<210> SEQ ID NO 30
<211> LENGTH: 28
<212> TYPE: DNA
<213> ORGANISM: Artificial Sequence
<220> FEATURE:
<223> OTHER INFORMATION: Cyclophilin A (cyclo) (accession number M19533)
      probe 02

<400> SEQUENCE: 30
atggtcaacc ccaccgtgtt cttcgaca                                     28
```

AZETIDINE DERIVATIVES USEFUL AS MODULATORS OF CORTICAL CATHECOLAMINERGIC NEUROTRANSMISSION

CROSS-REFERENCE TO RELATED APPLICATIONS

The application is a U.S. National Phase Application of International Application No. PCT/EP2016/061479, filed May 20, 2016, which claims priority to European Application No. 15168373.7, filed May 20, 2015, and Swedish Application No. 1650485-4, filed April 11, 2016, each of which are hereby incorporated by reference in their entirety.

REFERENCE TO SEQUENCE LISTING

The Sequence Listing submitted Nov. 16, 2017, as a text file named "37441_0023U1_Sequence_Listing.txt," created on Nov. 15, 2017, and having a size of 7,966 bytes is hereby incorporated by reference pursuant to 37 C.F.R. § 1.52(e)(5).

TECHNICAL FIELD

The present disclosure relates to novel 3-benzyl-azetidine derivatives, useful for modulating levels of monoamines, such as dopamine, norepinephrine and serotonin, in cerebral cortical areas of the mammalian brain, and more specifically for the treatment of central nervous system disorders. The present disclosure also relates to the use of these compounds in a method for therapy and to pharmaceutical compositions comprising the compounds of the present disclosure.

BACKGROUND

The cerebral cortex encompasses several major regions that are involved in higher functions such as thought, feelings, memory and planning. Monoamines, such as dopamine, norepinephrine and serotonin, are important as neurotransmitters for mammalian cortical function. The ascending serotonergic and noradrenergic pathways innervate virtually all regions of the brain including the cerebral cortex. The dopaminergic neurons of the CNS have more distinct projections, including the meso-cortical pathway primarily innervating the frontal cortex, in addition to a number of specific subcortical pathways. Primary or secondary dysfunctions in the activity of the monoamine pathways innervating the cerebral cortex lead to aberrations of the activity at cortical dopamine, norepinephrine and serotonin receptors and subsequently to manifestations of psychiatric and neurological symptoms.

The monoamines of the cortex modulate several aspects of cortical functions controlling affect, anxiety, motivation, cognition, attention, arousal and wakefulness. Thus, the catecholamines dopamine and norepinephrine exert strong influence on the frontal cortical areas, the integrity of which is essential for the so-called executive cognitive functions, related to e.g. attention, planning of actions and impulse control. Norepinephrine is a major part in the circuitry regulating anxiety and fear and is thus believed to be dysregulated in anxiety disorders such as panic disorders, generalized anxiety disorder (GAD) and specific phobias. Concerning mood and affective functions, the usefulness of compounds facilitating particularly norepinephrine and serotonin neurotransmission in the treatment of depression and anxiety has strongly contributed to the widely-accepted concept that these neuro-transmitters are both involved in the regulation of affective functions.

Hamon et al. (Prog Neuro-Psychopharm & Bio Psych, 2013, 45, 54-63) discloses that compounds specifically affecting the transmission of monoamines, more precisely norepinephrine, dopamine and serotonin, are successfully used to alleviate the affective, cognitive, or attentional symptoms in patients suffering from e.g. depression, anxiety and attention deficit hyperactivity disorder (ADHD). In addition, Arnsten (Biol Psych, 2011, 69(12); 89-99) discloses that all current pharmacological treatments for ADHD facilitate catecholamine transmission. Furthermore, Wang (Front Cell Neurosci, 2015, 9; 1-23) discloses that modulation of monoaminergic transmission has been suggested as a promising principle for the treatment of autism spectrum disorders.

Trillo et al. (Neurosci & Biobehav Rev, 2013, 37; 1363-79) discloses that in Alzheimer's disease, progressive degeneration of ascending monoamine systems have been linked to cognitive as well as non-cognitive symptoms, and pharmacological interventions leading to enhanced monoamine transmission have been suggested as a strategy both for symptomatic and disease-modifying treatments of Alzheimer's disease.

Furthermore, the monoamine systems in the cortex are known to be directly or indirectly involved in the core symptoms of schizophrenia. It has been proposed that this disorder emerges as various pathological etiologies converge upon cortical synaptic processes leading to dysregulation of the cortical micro-circuitry, which is clinically manifested as the symptoms of schizophrenia (Harrison et al., Mol Psych, 2005, 10; 40-68). This cortical microcircuitry is regulated by several neurotransmitters, including glutamate, GABA, and dopamine. It has further been proposed that pharmacological enhancement of cortical dopamine transmission could restore the function of this microcircuitry, providing a useful strategy for improved treatment of schizophrenia (Abi-Dargham et al., Eur Psych, 2005, 20; 15-27).

WO 2004/113297 discloses aza-ring derivatives and their use as monoamine neurotransmitter re-uptake inhibitors. EP 2754653 discloses azetidine derivatives and their use as monoamine neurotransmitter re-uptake inhibitors.

SUMMARY

An object of the present disclosure is to provide novel therapeutically active compounds, especially useful in treatment of disorders in the central nervous system. A further object is the provision of compounds for modulation of dopamine and norepinephrine neurotransmission in the mammalian brain, including human brain. A still further object is the provision of novel compounds with a cortical enhancer profile. A further object is to provide compounds with therapeutic effects after oral administration. A still further object is the provision of compounds with more optimal pharmacodynamic and pharmacokinetic properties such as e.g. plasma half-life, bioavailability, solubility and in vitro and in vivo efficacy. A further object is to provide compounds being superior to presently known compounds in the treatment of several disorders related to dysfunctions of the CNS, in terms of efficacy and/or side effects.

The present disclosure concerns the compounds as disclosed herein displaying certain effects on monoamines in the cerebral cortex, and the use of these compounds in the treatment for certain CNS disorders. Unexpectedly, it has been found that compounds of the present disclosure produce regionally selective increases in catecholamine levels in the frontal cortex but also increases in serotonin levels across brain regions, including frontal cortex. Due to the specific modulatory effects by the monoamines on cortical functions related to cognition, attention and affect, compounds as disclosed herein can be used in the treatment of disorders characterized by impairment of such functions. Thus, compounds as disclosed herein can be used in the treatment of cognitive, affective, and anxiety disorders. The compounds can also be used to treat symptoms of schizophrenia, which is characterized by dysfunctions of the cerebral cortex manifested in cognitive impairment and psychosis.

The present disclosure provides compounds of Formula I, including an enantiomer or mixture of enantiomers thereof, or a pharmaceutically acceptable salt thereof,

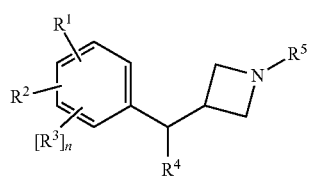

Formula I wherein
$R^1$ is F,
$R^2$ is F,
$R^3$ is F,
$R^4$ is F or $CH_3$,
$R^5$ is H or $C_1$-$C_4$alkyl substituted with 0, 1, 2 or 3 F, and
n is 0, 1, 2 or 3.

The present disclosure also provides a pharmaceutical composition, comprising a therapeutically effective amount of a compound of Formula I of the present disclosure, including any of its enantiomers or any mixture of its enantiomers, or a pharmaceutically acceptable salt thereof, together with at least one pharmaceutically acceptable carrier, excipient or diluent.

Further, there is also provided a compound of Formula I of the present disclosure, including any of its enantiomers or any mixture of its enantiomers, or a pharmaceutically acceptable salt thereof, for use as a medicament. The medicament may be a medicament for the treatment and/or prevention of a disease, disorder and/or condition in which disease, disorder or condition is responsive to modulation of monoamines in the cerebral cortex.

There is also provided a compound of Formula I as described herein, including any of its enantiomers or any mixture of its enantiomers, or a pharmaceutically acceptable salt thereof, for use in the treatment and/or prevention of a disease, disorder and/or condition in which disease, disorder or condition is responsive to modulation of monoamines in the cerebral cortex.

There is also provided a use of a compound of Formula I as described herein, including any of its enantiomers or any mixture of its enantiomers, or a pharmaceutically acceptable salt thereof, for the manufacture of a medicament for the use in the treatment and/or prevention of a disease, disorder and/or condition in which disease, disorder or condition is responsive to modulation of monoamines in the cerebral cortex.

There is also provided a method for treatment and/or prevention or alleviation of a disease, disorder and/or condition of a human, which disorder, disease or condition is responsive to modulation of monoamines in the cerebral cortex, which method comprises the step of administering to a human in need thereof a therapeutically effective amount of a compound of Formula I of the present disclosure, including any of its enantiomers or any mixture of its enantiomers, or a pharmaceutically acceptable salt thereof or therapeutically active metabolites of compounds as disclosed herein.

Other aspects of the present disclosure will be apparent to the person skilled in the art from the following detailed description and examples.

DETAILED DESCRIPTION

The following abbreviations will be used in the present disclosure:
NA: norepinephrine, NM: normetanephrine; DA: dopamine, DOPAC: 3,4-dihydroxyphenylacetic acid; 3-MT: 3-methoxytyramine; 5-HT: serotonin (5-hydroxytryptamine), TEA: triethylamine.

The present disclosure provides compounds of Formula I, including an enantiomer or mixture of enantiomers thereof, or a pharmaceutically acceptable salt thereof:

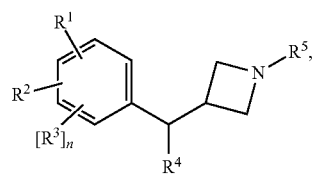

Formula I wherein
$R^1$ is F,
$R^2$ is F,
$R^3$ is F,
$R^4$ is F or $CH_3$,
$R^5$ is H or $C_1$-$C_4$alkyl substituted with 0, 1, 2 or 3 F, and
n is 0, 1, 2 or 3.

Since $R^1$, $R^2$ and $R^3$ are all F, compounds of Formula I may also be depicted as:

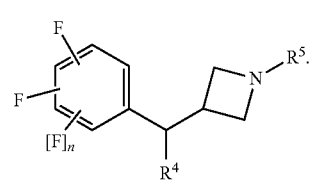

Formula I

In Formula I, n may have the value 0 or 1.

Compounds of Formula I for which n is 0 are compounds being substituted with two F on the phenyl ring. Thus, there is provided compounds of Formula II, including an enantiomer or a mixture of enantiomers thereof, or a pharmaceutically acceptable salt thereof:

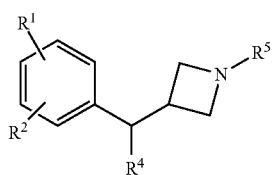

Formula II wherein $R^1$, $R^2$, $R^4$ and $R^5$ may have the values indicated for compounds of Formula I. Since $R^1$ and $R^2$ are F, compounds of Formula II may also be depicted as:

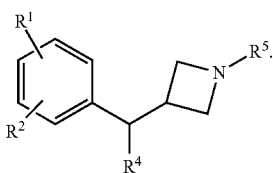

Formula II

Compounds of Formula II may be selected from the group consisting of compounds of Formula IIa, Formula IIb, Formula IIc, Formula IId, Formula IIe and Formula IIf, including an enantiomer or mixture of enantiomers thereof, and/or a pharmaceutically acceptable salt thereof:

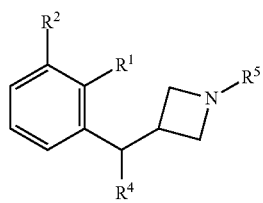

Formula IIa

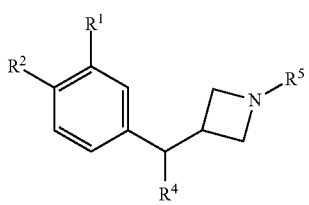

Formula IIb

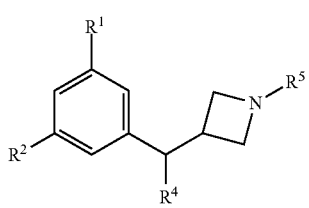

Formula IIc

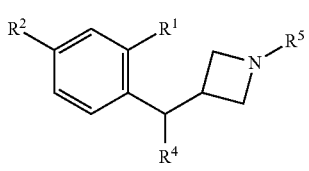

Formula IId

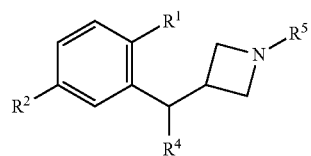

Formula IIe

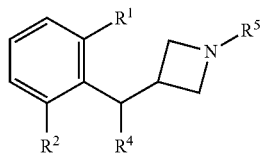

Formula IIf wherein $R^1$, $R^2$, $R^4$ and $R^5$ may have the values indicated for compounds of Formula I.

Since $R^1$ and $R^2$ are both F, compounds of Formula IIa, Formula IIb, Formula IIc, Formula IId, Formula IIe and Formula IIf may also be depicted as:

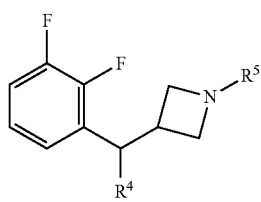

Formula IIa

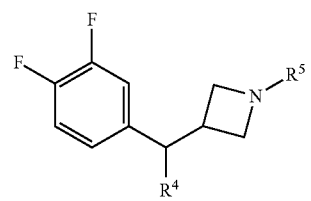

Formula IIb

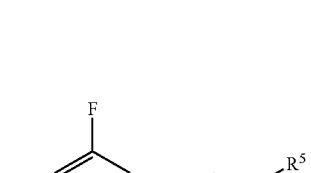

Formula IIc

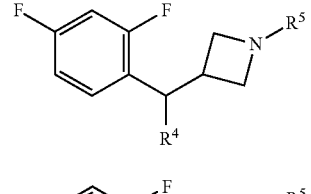

Formula IId

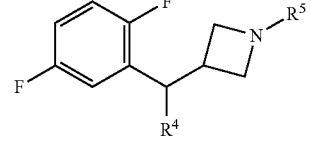

Formula IIe

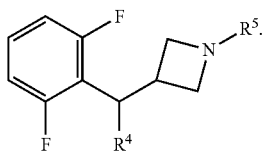

Formula IIf

In an example, $R^4$ may be F, and $R^5$ may be H thereby providing compounds of Formula II':

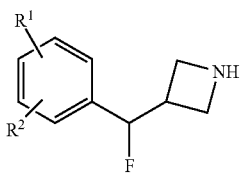

Formula II' wherein $R^1$ and $R^2$ are both F.

Since $R^1$ and $R^2$ are both F, compounds of Formula II' may also be depicted as:

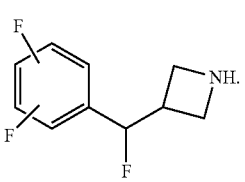

Formula II'

Compounds of Formula II' may be selected from the group consisting of compounds of Formula II'a, Formula II'b, Formula II'c, Formula II'd, Formula II'e and Formula II'f, including an enantiomer or mixture of enantiomers thereof, and/or a pharmaceutically acceptable salt thereof:

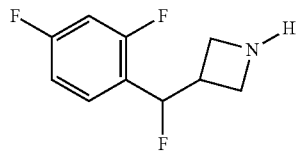

Formula II'a

Formula II'b

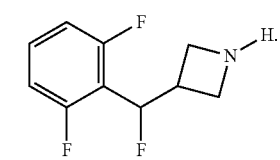

Formula II'c

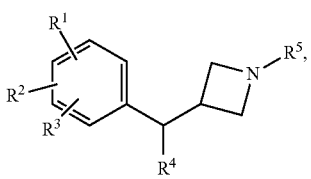

Formula II'd

Formula II'e

Formula II'f

Compounds of Formula I for which n is 1 are compounds being substituted with three F on the phenyl ring. Thus, there is provided compounds of Formula III, including an enantiomer or mixture of enantiomers thereof, or a pharmaceutically acceptable salt thereof:

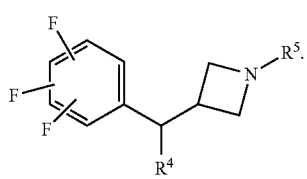

Formula III wherein $R^1$, $R^2$, $R^3$, $R^4$ and $R^5$ may have the values indicated for compounds of Formula I. Since $R^1$, $R^2$ and $R^3$ are all F, compounds of Formula III may also be depicted as:

Formula III

Compounds of Formula III may be selected from the group consisting of compounds of Formula IIIa, Formula IIIb, Formula IIIc, Formula IIId and Formula IIIe, an enantiomer or a mixture of enantiomers thereof, or a pharmaceutically acceptable salt thereof:

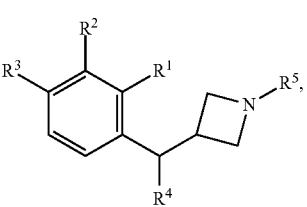

Formula IIIa

-continued

Formula IIIb

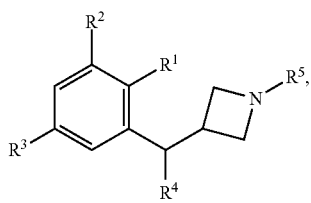

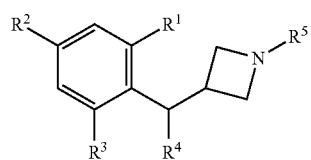

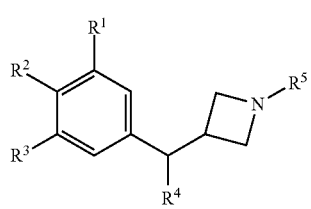

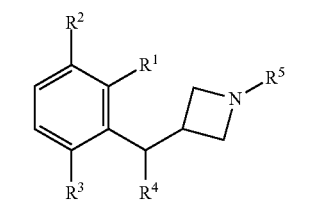

wherein $R^1$, $R^2$, $R^3$, $R^4$ and $R^5$ may have the values indicated for compounds of Formula I.

Since $R^1$, $R^2$ and $R^3$ are all F, compounds of Formula IIIa, Formula IIIb, Formula IIIc, Formula IIId and Formula IIIe may also be depicted as:

Formula IIIa

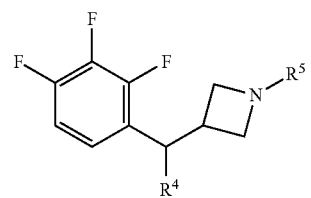

Formula IIIb

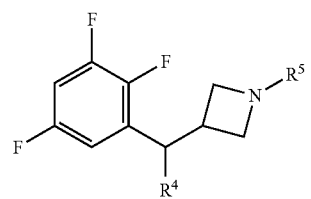

Formula IIIc

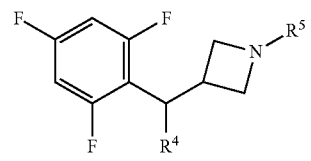

Formula IIId

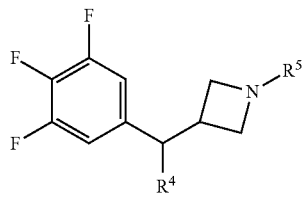

Formula IIIe

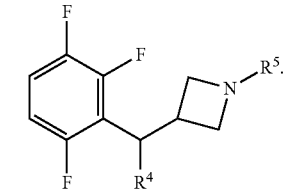

In compounds of Formula I, n may have the value 2 or 3.

Compounds of Formula I for which n is 2 are compounds being substituted with four F on the phenyl ring. Thus, there is provided compounds of Formula IVa, Formula IVb or Formula IVc, including an enantiomer or mixture of enantiomers thereof, or a pharmaceutically acceptable salt thereof:

Formula IVa

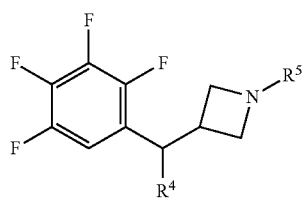

Formula IVb

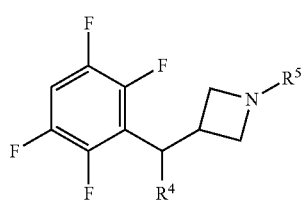

Formula IVc

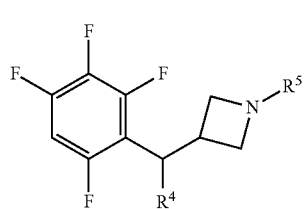

wherein $R^4$ and $R^5$ may have the values indicated for compounds of Formula I.

Compounds of Formula I for which n is 3 are compounds being substituted with five F on the phenyl ring. Thus, there is provided compounds of Formula V, including an enantiomer or mixture of enantiomers thereof, or a pharmaceutically acceptable salt thereof:

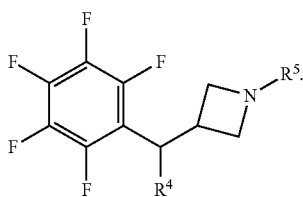

Formula V

There is also provided a compound as disclosed herein, wherein $R^4$ is F. Alternatively or additionally, there is provided a compound as disclosed herein, wherein $R^4$ is $CH_3$. For each of these $R^4$ values, $R^5$ may be H or $C_1$-$C_4$alkyl substituted with 0, 1, 2 or 3 F. In an example, the $C_1$-$C_4$alkyl substituted with 0, 1, 2 or 3 F may be selected from the group consisting of methyl, ethyl, propyl, isopropyl, cyclopropyl, n-butyl, sec-butyl, iso-butyl, tert-butyl and cyclobutyl. In a further example, the $C_1$-$C_4$alkyl substituted with 0, 1, 2 or 3 F may be selected from the group consisting of methyl, ethyl, propyl and n-butyl. $R^5$ may also be selected from the group consisting of hydrogen, methyl, ethyl, propyl, isopropyl, cyclopropyl, n-butyl, sec-butyl, iso-butyl, tert-butyl and cyclobutyl. Further, $R^5$ may be selected from the group consisting of hydrogen, methyl, ethyl, propyl, and n-butyl.

There is also provided a compound as disclosed herein, including an enantiomer or mixture of enantiomers, or a pharmaceutically acceptable salt thereof, wherein

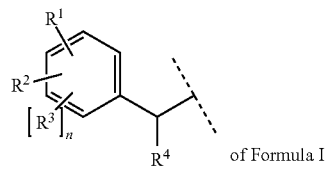

of Formula I is selected from the group consisting of:
3-[(2,3-DIFLUOROPHENYL)(FLUORO)METHYL],
3-[(3,5-DIFLUOROPHENYL)(FLUORO)METHYL],
3-[(3,4-DIFLUOROPHENYL)(FLUORO)METHYL],
3-[(2,5-DIFLUOROPHENYL)(FLUORO)METHYL],
3-[(2,6-DIFLUOROPHENYL)(FLUORO)METHYL],
3-[(2,4-DIFLUOROPHENYL)(FLUORO)METHYL],
3-[FLUORO(2,3,5-TRIFLUOROPHENYL)METHYL],
3-[FLUORO(2,4,6-TRIFLUOROPHENYL)METHYL],
3-[FLUORO(2,3,4-TRIFLUOROPHENYL)METHYL],
3-[FLUORO(3,4,5-TRIFLUOROPHENYL)METHYL],
3-[FLUORO(2,3,5,6-TETRAFLUORORPHENYL)METHYL], and
3-[FLUORO(PENTAFLUOROPHENYL)METHYL]
and
$R^5$ is selected from the group consisting of hydrogen, methyl, ethyl and propyl.

It shall be understood that as used herein all references to compounds of Formula I such as compounds of Formula II, Formula III, Formula IVa, Formula IVb, Formula IVc, Formula V and Formula VI are intended to include all possible pharmaceutically acceptable salts, co-crystals, solvates, hydrates, polymorphs, stereoisomers and tautomeric isomers thereof.

In addition, compounds of Formula I such as compounds of Formula II, Formula III, Formula IVa, Formula IVb, Formula IVc, Formula V and Formula VI may be administered in the form of a prodrug. A prodrug is a compound which may have little or no pharmacological activity itself, but when such compound is administered into or onto the body of a patient, it is converted into a compound of Formula I having the desired activity. Various prodrugs are known within the art (e.g. Rautio et al., Nat Rev Drug Discov, 2008, 7(3); 255-70).

Also included within the scope of the present disclosure are metabolites of compounds of Formula I such as compounds of Formula II, Formula III, Formula IVa, Formula IVb, Formula IVc, Formula V and Formula VI, that is compounds formed in vivo upon administration of compounds of Formula I.

The present disclosure provides a compound selected from:
(−)-3-[(2,3-DIFLUOROPHENYL)(FLUORO)METHYL] AZETIDINE,
(+)-3-[(2,3-DIFLUOROPHENYL)(FLUORO)METHYL] AZETIDINE,
(−)-3-[(3,5-DIFLUOROPHENYL)(FLUORO)METHYL] AZETIDINE,
(+)-3-[(3,5-DIFLUOROPHENYL)(FLUORO)METHYL] AZETIDINE,
3-[(3,4-DIFLUOROPHENYL)(FLUORO)METHYL]AZETIDINE,
3-[(2,5-DIFLUOROPHENYL)(FLUORO)METHYL]AZETIDINE,
3-[(2,6-DIFLUOROPHENYL)(FLUORO)METHYL]AZETIDINE,
3-[(2,4-DIFLUOROPHENYL)(FLUORO)METHYL]AZETIDINE,
3-[FLUORO(2,3,5-TRIFLUOROPHENYL)METHYL] AZETIDINE,
3-[FLUORO(2,4,6-TRIFLUOROPHENYL)METHYL] AZETIDINE,
3-[FLUORO(2,3,4-TRIFLUOROPHENYL)METHYL] AZETIDINE,
3-[FLUORO(3,4,5-TRIFLUOROPHENYL)METHYL] AZETIDINE,
3-[(3,5-DIFLUOROPHENYL)(FLUORO)METHYL]AZETIDINE,
3-[(2,3-DIFLUOROPHENYL)(FLUORO)METHYL]AZETIDINE,
3-[(2,3-DIFLUOROPHENYL)(FLUORO)METHYL]-1-ETHYLAZETIDINE,
3-[(2,3-DIFLUOROPHENYL)(FLUORO)METHYL]-1-PROPYLAZETIDINE,
3-[(3,5-DIFLUOROPHENYL)(FLUORO)METHYL]-1-METHYLAZETIDINE,
3-[(3,5-DIFLUOROPHENYL)(FLUORO)METHYL]-1-ETHYLAZETIDINE,
3-[(3,5-DIFLUOROPHENYL)(FLUORO)METHYL]-1-PROPYLAZETIDINE,
3-[FLUORO(2,3,5-TRIFLUOROPHENYL)METHYL]-1-METHYLAZETIDINE,
1-ETHYL-3-[FLUORO(2,3,5-TRIFLUOROPHENYL) METHYL]AZETIDINE,
3-[FLUORO(2,3,5-TRIFLUOROPHENYL)METHYL]-1-PROPYLAZETIDINE,
1-ETHYL-3-[FLUORO(2,3,4-TRIFLUOROPHENYL) METHYL]AZETIDINE,
3-[FLUORO(2,3,4-TRIFLUOROPHENYL)METHYL]-1-PROPYLAZETIDINE,
1-ETHYL-3-[FLUORO(3,4,5-TRIFLUOROPHENYL) METHYL]AZETIDINE,
3-[FLUORO(3,4,5-TRIFLUOROPHENYL)METHYL]-1-PROPYLAZETIDINE, 3-[FLUORO(2,3,5,6-TETRAFLUORORPHENYL)
   METHYL]AZETIDINE,
3-[FLUORO(Pentafluorophenyl)Methyl]Azetidine,
3-[FLUORO(2,3,5,6-TETRAFLUOROPHENYL)
   METHYL]-1-METHYLAZETIDINE,
1-ETHYL-3-[FLUORO(2,3,5,6-TETRAFLUOROPHE-
   NYL)METHYL]-AZETIDINE, and
3-[FLUORO(2,3,5,6-TETRAFLUOROPHENYL)
   METHYL]-1-PROPYLAZETIDINE
or a pharmaceutically acceptable salt of any of the foregoing compounds.

The present disclosure provides a compound selected from:
(−)-3-[(2,3-DIFLUOROPHENYL)(FLUORO)METHYL]
   AZETIDINE,
(+)-3-[(2,3-DIFLUOROPHENYL)(FLUORO)METHYL]
   AZETIDINE,
(−)-3-[(3,5-DIFLUOROPHENYL)(FLUORO)METHYL]
   AZETIDINE,
(+)-3-[(3,5-DIFLUOROPHENYL)(FLUORO)METHYL]
   AZETIDINE,
3-[(3,4-DIFLUOROPHENYL)(FLUORO)METHYL]AZE-
   TIDINE,
3-[(2,5-DIFLUOROPHENYL)(FLUORO)METHYL]AZE-
   TIDINE,
3-[(2,6-DIFLUOROPHENYL)(FLUORO)METHYL]AZE-
   TIDINE,
3-[(2,4-DIFLUOROPHENYL)(FLUORO)METHYL]AZE-
   TIDINE,
3-[FLUORO(2,3,5-TRIFLUOROPHENYL)METHYL]
   AZETIDINE,
3-[FLUORO(2,4,6-TRIFLUOROPHENYL)METHYL]
   AZETIDINE,
3-[FLUORO(2,3,4-TRIFLUOROPHENYL)METHYL]
   AZETIDINE,
3-[FLUORO(3,4,5-TRIFLUOROPHENYL)METHYL]
   AZETIDINE,
3-[(3,5-DIFLUOROPHENYL)(FLUORO)METHYL]AZE-
   TIDINE,
3-[(2,3-DIFLUOROPHENYL)(FLUORO)METHYL]AZE-
   TIDINE,
3-[FLUORO(2,3,5,6-TETRAFLUORORPHENYL)
   METHYL]AZETIDINE, and
3-[FLUORO(Pentafluorophenyl)Methyl]Azetidine
or a pharmaceutically acceptable salt of any of the foregoing compounds In a further example, there is provided a compound selected from:
3-[(2,3-DIFLUOROPHENYL)(FLUORO)METHYL]-1-
   METHYLAZETIDINE,
3-[(2,3-DIFLUOROPHENYL)(FLUORO)METHYL]-1-
   ETHYLAZETIDINE,
3-[(2,3-DIFLUOROPHENYL)(FLUORO)METHYL]-1-
   PROPYLAZETIDINE,
3-[(3,5-DIFLUOROPHENYL)(FLUORO)METHYL]-1-
   METHYLAZETIDINE,
3-[(3,5-DIFLUOROPHENYL)(FLUORO)METHYL]-1-
   ETHYLAZETIDINE,
3-[(3,5-DIFLUOROPHENYL)(FLUORO)METHYL]-1-
   PROPYLAZETIDINE,
3-[FLUORO(2,3,5-TRIFLUOROPHENYL)METHYL]-1-
   METHYLAZETIDINE,
1-ETHYL-3-[FLUORO(2,3,5-TRIFLUOROPHENYL)
   METHYL]AZETIDINE,
3-[FLUORO(2,3,5-TRIFLUOROPHENYL)METHYL]-1-
   PROPYLAZETIDINE,
1-ETHYL-3-[FLUORO(2,3,4-TRIFLUOROPHENYL)
   METHYL]AZETIDINE,
3-[FLUORO(2,3,4-TRIFLUOROPHENYL)METHYL]-1-
   PROPYLAZETIDINE,
1-ETHYL-3-[FLUORO(3,4,5-TRIFLUOROPHENYL)
   METHYL]AZETIDINE,
3-[FLUORO(3,4,5-TRIFLUOROPHENYL)METHYL]-1-
   PROPYLAZETIDINE,
3-[FLUORO(2,3,5,6-TETRAFLUOROPHENYL)
   METHYL]-1-METHYLAZETIDINE,
1-ETHYL-3-[FLUORO(2,3,5,6-TETRAFLUOROPHE-
   NYL)METHYL]-AZETIDINE, and
3-[FLUORO(2,3,5,6-TETRAFLUOROPHENYL)
   METHYL]-1-PROPYLAZETIDINE
or a pharmaceutically acceptable salt of any of the foregoing compounds.

There is also provided a compound selected from:
3-[FLUORO(2,3,5-TRIFLUOROPHENYL)METHYL]
   AZETIDINE,
3-[FLUORO(2,4,6-TRIFLUOROPHENYL)METHYL]
   AZETIDINE,
3-[FLUORO(2,3,4-TRIFLUOROPHENYL)METHYL]
   AZETIDINE,
3-[FLUORO(3,4,5-TRIFLUOROPHENYL)METHYL]
   AZETIDINE,
3-[FLUORO(2,3,5-TRIFLUOROPHENYL)METHYL]-1-
   METHYLAZETIDINE,
1-ETHYL-3-[FLUORO(2,3,5-TRIFLUOROPHENYL)
   METHYL]AZETIDINE,
3-[FLUORO(2,3,5-TRIFLUOROPHENYL)METHYL]-1-
   PROPYLAZETIDINE,
1-ETHYL-3-[FLUORO(2,3,4-TRIFLUOROPHENYL)
   METHYL]AZETIDINE,
3-[FLUORO(2,3,4-TRIFLUOROPHENYL)METHYL]-1-
   PROPYLAZETIDINE, and
3-[FLUORO(3,4,5-TRIFLUOROPHENYL)METHYL]-1-
   PROPYLAZETIDINE
or a pharmaceutically acceptable salt of any of the foregoing compounds.

Examples of specific compounds according to Formula II' are:
(±)-3-[(2,3-difluorophenyl)(fluoro)methyl]azetidine;
(±)-3-[(3,5-difluorophenyl)(fluoro)methyl]azetidine;
(±)-3-[(3,4-difluorophenyl)(fluoro)methyl]azetidine;
or a pharmaceutically acceptable salts of any of the foregoing compounds.

Further, examples of specific compounds according to Formula II' are:
(+)-3-[(2,3-difluorophenyl)(fluoro)methyl]azetidine;
(−)-3-[(2,3-difluorophenyl)(fluoro)methyl]azetidine;
(+)-3-[(3,5-difluorophenyl)(fluoro)methyl]azetidine;
(−)-3-[(3,5-difluorophenyl)(fluoro)methyl]azetidine;
(+)-3-[(3,4-difluorophenyl)(fluoro)methyl]azetidine;
(−)-3-[(3,4-difluorophenyl)(fluoro)methyl]azetidine;
or a pharmaceutically acceptable salts of any of the foregoing compounds.

There is also provided a compound as disclosed herein in the form of a (+)-enantiomer. Further, there is provided a compound as disclosed herein in the form of a (−)-enantiomer.

It is believed that compounds of the present disclosure possess satisfactory pharmacological profile and promising biopharmaceutical properties, such as toxicological profile, metabolism and pharmacokinetic properties, solubility and permeability, in particular for providing a satisfactory bioavailability upon oral administration thereof.

Compounds of the present disclosure may have advantageous properties compared to compounds of prior art, such as enhanced potency and/or enhanced selectivity. Such advantages may provide for corresponding useful properties in practice. For example, when used as a medicament, compounds of Formula I may have a lower daily clinical dose, longer duration of action and/or an improved side effect profile compared to compounds of prior art.

Monosubstituted Compounds

The present disclosure also encompasses compounds in which $R^1$ is H, i.e. compounds in which the phenyl ring only carries one substituent. Thus, there is provided compounds of Formula VI, including an enantiomer or mixture of enantiomers, or a pharmaceutically acceptable salt thereof:

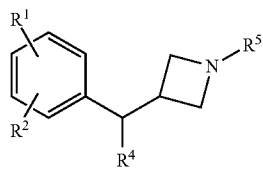

Formula VI wherein
$R^1$ is H,
$R^2$ is F
$R^4$ is F or $CH_3$, and
$R^5$ is H or $C_1$-$C_4$alkyl substituted with 0, 1, 2 or 3 F.

Since $R^1$ is H and $R^2$ is F, compounds of Formula VI may be depicted as:

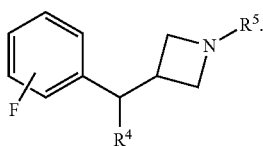

Formula VI

For instance, when $R^4$ is F and $R^5$ is H, there is provided compounds of Formula VI':

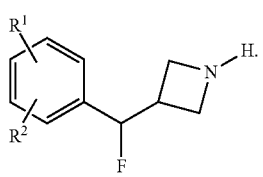

Formula VI'

Compounds of Formula VI' may also be depicted as:

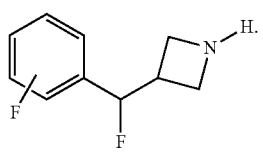

Formula VI'

Compounds of Formula VI may be selected from the group consisting of compounds of Formula VIa, Formula VIb and Formula VIc:

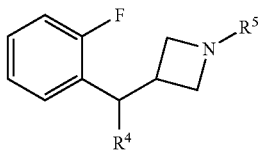

Formula VIa

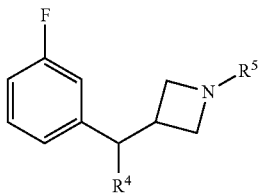

Formula VIb

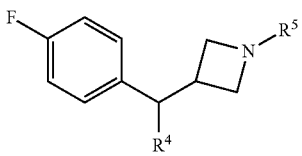

Formula VIc wherein
$R^4$ is F or $CH_3$, and
$R^5$ is H or $C_1$-$C_4$alkyl substituted with 0, 1, 2 or 3 F.

In an example, $R^4$ may be F and $R^5$ may be H for compounds of Formula VIa, Formula VIb and/or Formula VIc. In a particular example, $R^4$ may be F and $R^5$ may be H for compounds of Formula VIb.

Pharmaceutically Acceptable Salts

Compounds of the present disclosure may be provided in any form suitable for the intended administration. Suitable forms include pharmaceutically (i.e. physiologically) acceptable salts of a compound as disclosed herein (Paulekuhn G S et al., J Med Chem, 2007, 50; 6665-72 and Berge S M et al., J Pharm Sci, 1977, 66; 1-19). As used herein "pharmaceutically acceptable salt", where such salts are possible, includes salts prepared from pharmaceutically acceptable non-toxic acids, i.e. pharmaceutically acceptable acid addition salts.

Examples of pharmaceutically acceptable salts include, without limitation, non-toxic inorganic and organic acid addition salts such as hydrochloride, hydrobromide, borate, nitrate, perchlorate, phosphate, sulphate, formate, acetate, aconate, ascorbate, benzenesulphonate, benzoate, cinnamate, citrate, embonate, enantate, fumarate, glutamate, glycolate, lactate, maleate, malonate, mandelate, methanesulphonate, naphthalene-2-sulphonate, phthalate, propionate, salicylate, sorbate, stearate, succinate, tartrate, toluene-p-sulphonate, and the like. Hemisalts of acids may also be formed, for example, hemisulphate. Such salts may be formed by procedures well known and described in the art.

Other acids such as oxalic acid, which may not be considered pharmaceutically acceptable, may be useful in the preparation of salts useful as intermediates in obtaining a compound of the present disclosure and its pharmaceutically acceptable acid addition salt.

Co-crystals

In a salt, proton transfer may occur between the active pharmaceutical ingredient and the counter ion of the salt. However, in some cases there is no or only partial proton transfer and the solid is therefore not a true salt. It is accepted that the proton transfer is in fact a continuum, and can change with temperature, and therefore the point at which a salt is better described as a "co-crystal" may be subjective. The term "co-crystal" as used herein refers to multicomponent system in which there exists a host molecule or molecules (active pharmaceutical ingredient) and a guest (or co-former) molecule or molecules. The guest or co-former molecule is defined as existing as a solid at room temperature in order to distinguish the co-crystal from solvates. However, a co-crystal may itself form solvates. In a co-crystal there is generally predominance for interaction through non-ionic forces, such as hydrogen bonding.

Solvates

It is also to be understood that certain compounds of the present disclosure may exist in solvated forms, including solvates of the free compounds or solvates of a salt of the compound, as well as in unsolvated forms. The term "solvate" is used herein to describe a molecular complex comprising the compound of the present disclosure and one or more pharmaceutically acceptable solvent molecules, for example, ethanol. The term "hydrate" is employed when said solvent is water. Thus, solvated forms may include hydrated forms such as monohydrate, dihydrate, hemihydrate, trihydrate, tetrahydrate, and the like.

Polymorphs

Compounds of the present disclosure may exist in a continuum of solid states ranging from fully amorphous to fully crystalline. Thus, it is to be understood that all polymorphs, such as mixtures of different polymorphs, are included within the scope of the claimed compounds.

Isomers

It will be appreciated by those skilled in the art that compounds disclosed herein may exist in different enantiomeric forms. Compounds of the present disclosure include all such enantiomers, racemic mixtures thereof as well as mixtures in different proportions of the separate enantiomers.

Racemic forms can be resolved into the optical antipodes by known methods and techniques. One way of separating the enantiomeric compounds (such as enantiomeric intermediates) is—in the case the compound being a chiral base—by use of an optically active acid, and liberating the enantiomeric, resolved salt, by treatment with a base. Another method for resolving racemates into the optical antipodes is based upon chromatography on an optical active matrix. Racemic compounds of the present disclosure can thus be resolved into their optical antipodes, e.g., by fractional crystallization of D- or L-tartrates, mandelates, or camphor-sulphonate salts for example.

Compounds disclosed herein may also be resolved by the formation of diastereomeric amides by reaction of the chemical compounds of the present disclosure with an optically active activated carboxylic acid such as that derived from (+) or (−) phenylalanine, (+) or (−) phenylglycine, (+) or (−) camphanic acid or by the formation of diastereomeric carbamates by reaction of a compound of the present disclosure with an optically active chloroformate or the like.

Labelled Compounds

Compounds of the present disclosure may be used in their labelled or unlabeled form. In the context of this present disclosure the labelled compound has one or more atoms replaced by an atom having an atomic mass or mass number different from the atomic mass or mass number usually found in nature. The labelling will allow easy quantitative detection of said compound.

Labelled compounds of the present disclosure may be useful as diagnostic tools, radio tracers, or monitoring agents in various diagnostic methods, and for in vivo receptor imaging.

Labelled compounds of the present disclosure may contain at least one radio-nuclide as a label. Positron emitting radionuclides are all candidates for usage. In the context of this present disclosure the radionuclide may be selected from isotopes of hydrogen, carbon, nitrogen, fluorine and oxygen, such as 2H (deuterium), 3H (tritium), 11C, 13C, 14C, 18O, 17O, 19F and 18F. It is known that substitution with heavier isotopes, such as substitution of one or more hydrogen atoms with deuterium (2H) might provide pharmacological advantages in some instances, such as increased metabolic stability.

The physical method for detecting a labelled compound of the present disclosure may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), or combinations thereof.

Methods of Preparation

Compounds of the present disclosure may be prepared by conventional methods for chemical synthesis, e.g. those described in the working examples. The starting materials for the processes described in the present application are known or may readily be prepared by conventional methods from commercially available chemicals.

Also one compound of the present disclosure can be converted to another compound of the present disclosure using conventional methods.

The end products of the reactions described herein may be isolated by conventional techniques, e.g. by extraction, crystallization, distillation, chromatography, etc.

Persons skilled in the art will appreciate that, in order to obtain compounds of the present disclosure in an alternative—and in some occasions, more convenient manner—the individual process steps mentioned hereinbefore may be performed in a different order, and/or the individual reactions may be performed at different stage in the overall route (i.e. chemical transformations may be performed upon different intermediates to those associated hereinbefore with a particular reaction).

Description of Animal Models Used

The change in turnover of dopamine in the terminal areas of the ascending dopaminergic projections of the mammalian brain can be illustrated by measuring of changes in biochemical indices in the brain e.g. changes in concentrations of dopamine metabolites such as 3,4-dihydroxyphenylacetic acid (DOPAC) in the striatum and frontal cortex.

The measurement of the tissue content of DOPAC is well established in the field of research since the 1960's. In short, male Sprague-Dawley rats are administered the test compound 60 minutes prior to decapitation. The brain is rapidly taken out and dissected. The striatum is rapidly frozen and subsequently quantitatively analyzed with respect to its content of DOPAC by means of HPLC and electrochemical detection. The number of animals used for each test compound/vehicle is 5/group.

The microdialysis technique (See, for instance, Collin and Ungerstedt, Microdialysis: user's guide, Carnegie Medicin, Stockholm, 1988) is a well-established technique for measuring extracellular levels of neurotransmitters (Ungerstedt, J Int Med, 1991, 230; 365-73). The microdialysis technique was used to measure the effect of compounds disclosed herein upon the efflux of monoamine transmitters (NA, DA and 5-HT) in striatum and frontal cortex in conscious, freely moving rats.

Sesack et al. (Anatom Substr Glut-Dopamine Inter. Annals of NY AcadSci, 2003, 1003; 36-52) discloses that the dopaminergic systems of the brain interact strongly with central glutamate neurotransmission. To investigate potential effects of compounds as disclosed herein on cortical and striatal NMDA type glutamate receptor related synaptic signaling, Arc mRNA induction was assessed upon acute administration. Arc (Arc/Arg3.1-activity regulated cytoskeleton-associated protein/activity-regulated gene 3.1; (Link W et al., Proc Natl Acad Sci, USA, 1995, 92; 5734-8 and Lyford G L et al., Neuron, 1995, 14; 433-45), is an immediate early gene (IEG), induced by synaptic activity, whose expression and localization at synaptic sites is triggered specifically by NMDA receptor activation and strongly related to neural plasticity (Steward and Worley, Neuron, 2001, 30; 227-40, Kawashima et al., PNAS, 2009, 106(1); 316-21 and Bramham et al., Exp Brain Res, 2010, 200; 125-40).

The effect of compounds in the present disclosure on locomotor activity in drug-naïve rats was also investigated. The animals were placed in the motility meters immediately after drug administration and locomotor activity was recorded for 60 minutes (counts/60 min±SEM). The results are presented as percent of control.

Biological Activity

Compounds as disclosed herein possess modulating effects on monoamines in cerebral cortex and both they and their pharmaceutical compositions are useful in treating numerous central nervous system disorders such as psychiatric disorders. Particularly, compounds as disclosed herein and their pharmaceutical compositions are useful in the treatment of CNS disorders where the cortical monoaminergic systems are dysfunctional due to direct or indirect causes. Compounds according to the present disclosure can be used to treat affective disorders and cognitive disorders such as neurodegenerative and neurodevelopmental disorders and/or diseases. Also, compounds with modulating effects on dopaminergic systems may be used to improve motor functions in patients suffering from movement disorders.

Compounds with modulating effects on monoamines in cerebral cortex may be used to improve motor and cognitive functions and in the treatment of emotional disturbances related to ageing, neurodegenerative disorders and/or diseases (e.g. Alzheimer's disease, frontotemporal dementia, age-related cognitive impairment and vascular dementia) and developmental disorders (such as Autism spectrum disorders, ADHD, Cerebral Palsy, Gilles de la Tourette's syndrome) as well as after brain injury. Such brain injury may be induced by traumatic, inflammatory, infectious, neoplastic, vascular, hypoxic or metabolic causes or by toxic reactions to exogenous chemicals, wherein the exogenous chemicals are selected from the group consisting of substances of abuse, pharmaceutical compounds, environmental compounds and pharmaceutical compositions according to the present disclosure may also be used in behavioural disorders usually first diagnosed in infancy, childhood, or adolescence as well as in impulse control disorders.

Mood and anxiety disorders, depression and obsessive-compulsive disease may also be treated with compounds and compositions according to the present disclosure.

Compounds of the present disclosure may be used for treating substance abuse disorders as well as disorders characterized by misuse of food. Compounds of the present disclosure are further useful for treatment of a condition selected from the group consisting of sleep disorders, sexual disorders, eating disorders, obesity, and headaches and other pains in conditions characterized by increased muscular tone.

Neurological indications include the use of compounds disclosed herein and their pharmaceutical compositions to improve mental and motor function in Parkinson's disease, and in related parkinsonian syndromes, dyskinesias (such as L-DOPA induced dyskinesias) and dystonias. Compounds disclosed herein may also be used to ameliorate tics and tremor of different origins. Moreover, compounds disclosed herein may be used to relieve pain in conditions characterized by increased muscle tone.

The compounds disclosed herein can also be used in the treatment of Huntington's disease and other movement disorders as well as movement disorders induced by drugs. Restless legs and related disorders as well as narcolepsy may also be treated with compounds according to the present disclosure.

Compounds disclosed herein are considered useful for the treatment and/or prevention of all forms of psychosis, such as schizophrenia and schizophreniform and bipolar disorders as well as drug induced psychotic disorders. Iatrogenic and non-iatrogenic psychoses and hallucinoses may also be treated.

Pharmaceutical Compositions

There is also provided a pharmaceutical composition comprising a therapeutically effective amount of a compound of the present disclosure, or a pharmaceutically acceptable salt thereof, and at least one pharmaceutically acceptable carrier, excipient or diluent.

As used herein, the term "therapeutically effective amount" means an amount of a compound as disclosed herein that is sufficient to induce the desired therapeutic effect in a patient to which the compound is administered.

The present disclosure relates to a pharmaceutical composition comprising a compound of the present invention, and its use in treating CNS disorders. Both organic and inorganic acids can be employed to form non-toxic, pharmaceutically acceptable, acid addition salts of compounds according to the present disclosure. Suitable acid addition salts of compounds of the present disclosure include those formed with pharmaceutically acceptable salts such as those mentioned above. The pharmaceutical composition comprising a compound according to the present disclosure may also comprise excipients used to facilitate the production of the pharmaceutical preparation or the administration of the preparations. Such excipients are well known to people skilled in the art and may for instance be pharmaceutically acceptable adjuvants, diluents, carriers and preservatives.

In clinical practice, compounds according to the present disclosure will normally be administered orally, rectally, nasally or by injection, in the form of a pharmaceutical preparation comprising the active ingredient either as a free base or as a pharmaceutically acceptable non-toxic salt, such as an acid addition salt, e.g. hydrochloride, lactate, acetate or sulfamate salt, in association with a pharmaceutically acceptable carrier, excipient or diluent. The carrier, excipient or diluent may be a solid, semisolid or liquid preparation. Usually the active substance will constitute between 0.1 and 99% by weight of the preparation, more specifically between 0.5 and 20% by a weight for preparations intended for injection and between 0.2 and 50% by weight for preparations suitable for oral administration.

To produce pharmaceutical preparations containing a compound according to the present disclosure in the form of dosage units for oral application, the selected compound may be mixed with a solid excipient, e.g. lactose, saccharose, sorbitol, mannitol, starches such as potato starch, corn starch or amylopectin, cellulose derivatives, a binder such as gelatine or polyvinyl-pyrrolidine, and a lubricant such as magnesium stearate, calcium stearate, polyethylene glycol, waxes, paraffin, and the like, and then compressed into tablets. If coated tablets are required, the cores (prepared as described above) may be coated with a concentrated sugar solution which may contain e.g. gum arabic, gelatine, talcum, titanium dioxide, and the like. Alternatively, the tablet can be coated with a polymer known to the man skilled in the art, dissolved in a readily volatile organic solvent or mixture of organic solvents. Dyestuffs may be added to these coatings in order to readily distinguish between tablets containing different active substances or different amounts of the active compound.

For the preparation of soft gelatine capsules, the compound may be admixed with e.g. a vegetable oil or polyethylene glycol. Hard gelatine capsules may contain granules of the active substance using either the mentioned excipients for tablets e.g. lactose, saccharose, sorbitol, mannitol, starches (e.g. potato starch, corn starch or amylopectin), cellulose derivatives or gelatine. Also liquids or semisolids of the drug can be filled into hard gelatine capsules.

Examples of immediate release tablet and capsule formulations suitable for oral administration are given below:

| Tablet I | mg/tablet |
| --- | --- |
| Compound | 100 |
| Lactose Ph. Eur | 182.75 |
| Croscarmellose sodium | 2.0 |
| Maize starch paste (5% w/v paste) | 2.25 |
| Magnesium stearate | 3.0 |

| Tablet II | mg/tablet |
| --- | --- |
| Compound | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| Tablet III | mg/tablet |
| --- | --- |
| Compound | 1.0 |
| Lactose Ph. Eur | 93.25 |
| Croscarmellose sodium | 4.0 |
| Maize starch paste (5% w/v paste) | 0.75 |
| Magnesium stearate | 1.0 |

| Capsule | mg/capsule |
| --- | --- |
| Compound | 10 |
| Lactose Ph. Eur | 488.5 |
| Magnesium | 1.5 |

Dosage units for rectal application can be solutions or suspensions or can be prepared in the form of suppositories comprising the active substance in a mixture with a neutral fatty base, or gelatin rectal capsules comprising the active substance in admixture with vegetable oil or paraffin oil. Liquid preparations for oral application may be in the form of syrups or suspensions, for example solutions containing from about 0.2% to about 20% by weight of the active substance herein described, the balance being sugar and mixture of ethanol, water, glycerol and propylene glycol. Optionally such liquid preparations may contain colouring agents, flavouring agents, saccharine and carboxymethylcellulose as a thickening agent or other excipients known to the man in the art.

Solutions for parenteral applications by injection can be prepared in an aqueous solution of a water-soluble pharmaceutically acceptable salt of the active substance, preferably in a concentration of from 0.5% to about 10% by weight. These solutions may also containing stabilizing agents and/or buffering agents and may conveniently be provided in various dosage unit ampoules. The use and administration to a patient to be treated would be readily apparent to an ordinary skill in the art.

For intranasal administration or administration by inhalation, the compounds of the present invention may be delivered in the form of a solution, dry powder or suspension. Administration may take place via a pump spray container that is squeezed or pumped by the patient or through an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. Compounds of the invention may also be administered via a dry powder inhaler, either as a finely divided powder in combination with a carrier substance (e.g. a saccharide) or as microspheres. The inhaler, pump spray or aerosol spray may be single or multi dose. The dosage may be controlled through a valve that delivers a measured amount of active compound.

Compounds of the present disclosure may also be administered in a controlled release formulation. The compound is then released at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. The compounds may also be formulated in controlled release formulations in which release of the active compound is targeted. For example, release of the compound may be limited to a specific region of the digestive system through the pH sensitivity of the formulation. Such formulations are well known to persons skilled in the art.

Depending upon the disorder and patient to be treated and the route of administration, the compositions may be administered at varying doses. The dosing will also depend upon the relation of potency to absorbability and the frequency and route of administration. Such doses may be administered once, twice or three or more times daily. The compounds of this invention can be administered to subjects in doses ranging from 0.01 mg to 500 mg per kg of body weight per day, although variations will necessarily occur depending upon the weight, sex and condition of the subject being treated, the disease state being treated and the particular route of administration chosen. However, a dosage level that is in the range of from 0.1 mg to 10 mg per kg of body weight per day, single or divided dosage is most desirably employed in humans for the treatment of diseases. Alternatively, the dosage level is such that a serum concentration of between 0.1 nM to 10 µM of the compound is obtained.

Further, there is provided a compound of as disclosed herein and/or the specific compounds as exemplified herein, or a pharmaceutically acceptable salt thereof, for use in the treatment and/or prevention of a disease, disorder and/or condition which is responsive to modulation of monoamines in the cerebral cortex.

There is also provided a use of a compound disclosed herein and/or the specific compounds as exemplified herein, or a pharmaceutically acceptable salt thereof, for the manufacture of a medicament for the treatment and/or prevention of a disease, disorder and/or condition which is responsive to modulation of monoamines in the cerebral cortex. Alternatively or additionally, the disease, disorder and/or condition may be as described elsewhere in this document.

There is also provided a method for treatment and/or prevention of a disease, disorder and/or condition which is responsive to modulation of monoamines in the cerebral cortex, which method comprises the step of administering a therapeutically effective amount of a compound as disclosed herein and/or the specific compounds as exemplified herein, or a pharmaceutically acceptable salt thereof, to a patient in need thereof. Alternatively or additionally, the disease, disorder and/or condition may be as described elsewhere in this document.

There is also provided a use of a compound a and/or the specific compounds as exemplified herein, or a pharmaceutically acceptable salt thereof, for the manufacture of a medicament for the treatment and/or prevention of the disease, disorder and/or condition that may be selected from the group consisting of dementia, age-related cognitive impairment, neurodegenerative related cognitive disorders and/or diseases, autism spectrum disorders, attention deficit hyperactivity disorder (ADHD), affective disorders, depression, schizophrenia, anxiety disorders, and panic disorder. Alternatively or additionally, the disease, disorder and/or condition may be as described elsewhere in this document.

For instance, the disease, disorder and/or condition may be selected from the group consisting of dementia, age-related cognitive impairment, cognitive impairment associated with neurodegenerative disorders and/or diseases, autism spectrum disorders, attention deficit hyperactivity disorder (ADHD), affective disorders, schizophrenia, anxiety disorders and movement disorders. Examples of dementia include Alzheimer's disease and frontotemporal dementia. Examples of autism spectrum disorders include autism and Asperger's syndrome. Examples of affective disorders include major depression disorder, bipolar disorder and depression. Examples of anxiety disorders include panic disorder, generalized Anxiety Disorder (GAD) and social phobia. Examples of movement disorders include Parkinson's disease and Huntington's disease. Alternatively or additionally, the disease, disorder and/or condition may be as described elsewhere in this document.

In a further example, the disease, disorder and/or condition may be selected from the group consisting of dementia, age-related cognitive impairment, cognitive impairment associated with neurodegenerative disorders and/or diseases, autism spectrum disorders, affective disorders, schizophrenia, anxiety disorders, attention deficit hyperactivity disorder (ADHD) and movement disorders. In still a further example, the disease, disorder and/or condition may be selected from the group consisting of dementia, age-related cognitive impairment and schizophrenia.

In this document, treatment and/or prevention of a disease, disorder and/or condition may involve alleviation of symptoms associated with said disease, disorder and/or condition. For instance, the alleviation of symptoms may be reduction of the symptoms or rendering the symptoms less difficult.

Combination Therapy

One or more compounds as disclosed herein, such as a compound of Formula I, Formula II, Formula II', Formula III, Formula IVa, IVb, IVc, Formula V or Formula VI, may be combined with at least one other therapeutically active agent, said therapeutically active agent being is useful in the treatment and/or prevention of a disease, disorder and/or a condition which is responsive to modulation of monoamines in the cerebral cortex. For instance, the disease, disorder or condition may be selected from the group consisting of dementia, age-related cognitive impairment, neurodegenerative related cognitive disorders and/or diseases, autism spectrum disorders, attention deficit hyperactivity disorder (ADHD), affective disorders, depression, schizophrenia, anxiety disorders, and panic disorder. Alternatively or additionally, the disease, disorder and/or condition may be as described elsewhere in this document.

The combination of one or more compounds as disclosed herein with the at least one other therapeutically active agent may be provided as a single composition. Alternatively, the combination may be provided as a kit of parts.

Thus, there is provided a kit of parts comprising or consisting of:
(i) a compound as disclosed herein, and
(ii) a therapeutically active agent, said therapeutically active agent being is useful in the treatment, prevention or alleviation of a disease or a disorder or a condition which is responsive to modulation of monoamines in the cerebral cortex.

The compound of component (i) of the kit of parts may be provided together with a pharmaceutically acceptable carrier, excipient and/or diluent. Further, the therapeutically active agent of component (ii) of the kit of parts may be provided together with a pharmaceutically acceptable carrier, excipient and/or diluent.

The kit of parts may further comprise instructions for use, such as instructions for simultaneous, sequential or separate administration of the compound of component (i) and the therapeutically active agent of component (ii) of the kit of parts.

There is also provided a combination such as a single composition or a kit of parts as disclosed herein for use as a medicament.

Further, there is provided a combination such as a single composition or a kit of parts as disclosed herein for use in the treatment and/or prevention of a disease, disorder or condition which is responsive to modulation of monoamines in the cerebral cortex.

Further, there is provided a combination such as a single composition or a kit of parts as disclosed herein for use in the manufacture of a medicament for the treatment of a disease, disorder and/or condition which is responsive to modulation of monoamines in the cerebral cortex.

Further, there is provided a method of treatment of a disease, disorder and/or condition which is responsive to modulation of monoamines in the cerebral cortex, said method comprising the administration of an effective amount of of such as a single composition or the components of a kit of parts as disclosed herein to a patient in need thereof.

It will be appreciated that the compound of component (i), and the therapeutically agent of component (ii) of the kit of parts disclosed herein may be administered simultaneously, sequentially or separately.

Further, it will be appreciated in the context of the combination such as the single composition or the kit of parts disclosed herein that the disease, disorder and/or condition may be selected from the group consisting of dementia, age-related cognitive impairment, neurodegenerative related cognitive disorders and/or diseases, autism spectrum disorders, attention deficit hyperactivity disorder (ADHD), affective disorders, depression, schizophrenia, anxiety disorders, and panic disorder. Alternatively or additionally, the disease, disorder or condition may be as described elsewhere in this document.

EXAMPLES

The invention is further illustrated in the examples below and as outlined below, which in no way are intended to limit the scope of the invention.

The following general experimental procedures were used:
(i) Low resolution mass spectra were recorded on a HP 5970A instrument operating at an ionization potential of 70 eV. The mass detector was interfaced with a HP5700 gas chromatograph equipped with a HP-5MS UI GC column (15 m, 0.25 mm, 0.25 µm) with He gas flow 40 cm/s.
(ii) NMR experiments were run on a Oxford 800 magnet, Bruker Avance III HD spectrometer with 4 channels, 5 mm TXO cold probe and ASTM 13C S/N 3300. *Protons from fumaric acid counter ion.
(iii) Melting points were determined by a Buchi B-545 and are uncorrected.
(iv) For flash chromatography, Biotage Isolera Vers 1.2 with SNAP Cartridge KP-Sil, mobile phase gradient mixtures of isooctane/ethyl acetate/methanol was used.
(v) Separation of enantiomers were performed using a Kromasil 10-Cellucoat with mobile phase (heptane/2-propanol/diethyl amine, 98:2:0.1), sampling at 255-265 nm measured with Merck HITACHI UV-detector 1-7400 (single wavelength) on a Nova Prep 200 instrument. Analysis of enantiomeric purity was quantified by a Kromasil 5-cellucoat CT8031 column (4.6*250 mm) using a Gynotek single wavelength UV detector with Chromeleon v.6.8 software. Optical rotation was measured on a Perkin-Elmer 241 Polarimeter using a Na589 lamp (60-80 pAmp/5 sec integration).
(vi) Evaporation of solvents was performed using a Laborota 4000 connected to a Vario PC2001 vacuum pump.

The naming of compounds as disclosed herein was made using the software package J Chem for Excel, ver. 14.8.2600.753. In this document, if the chemical name and the chemical structure are inconsistent the chemical structure should be considered to be correct.

Example 1

(−)-3-[(2,3-Difluorophenyl)(Fluoro)Methyl]Azetidine Hydrochloric Acid Salt (−)-Enantiomer of

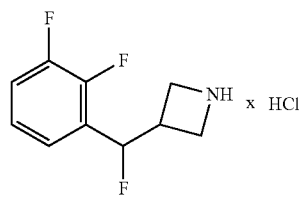 [SMILES: Fc1cccc(C(F)C2CNC2)c1F ; Cl]

(−)-Tert-butyl 3-[(2,3-difluorophenyl)(fluoro)methyl]azetidine-1-carboxylate (E1) (1.30 g, 4.32 mmol) was dissolved in methylene chloride (30 ml) and trifluoroacsetic acid (3 ml) was added where after the mixture was stirred at ambient temperature for 15 h. The solvent was evaporated and the crude product was added to a SCX-3 SPE-column, washed with Methanol and extracted with Methanol/TEA in a 4:1 ratio. The solvents were evaporated and the crude product (0.55 g, 2.73 mmol) was dissolved in 5 ml Ethanol and hydrochloric acid in Ethanol (1.25 M, 3.5 ml) was added. The solvent was evaporated and the crude salt (title compound) was recrystallized from 2-propanol: M.p. 149-150° C. (HCl). MS m/z (relative intensity, 70 eV) 201 (M+, 3), 171 (43), 153 (bp), 151 (44), 145 (38). $^1$H NMR (800 MHz, MeOD) δ ppm 3.45-3.56 (m, 1 H) 4.00-4.11 (m, 2 H) 4.11-4.19 (m, 1 H) 4.14 (dd, J=17.12, 10.27 Hz, 1 H) 5.95-6.10 (m, 1 H) 7.26 (d, J=2.93 Hz, 1 H) 7.29-7.37 (m, 1 H). $[\alpha]_D$=−28.1° (measured on the base with conc. 10 mg/ml).

Example 2

(+)-3-[(2,3-Difluorophenyl)(Fluoro)Methyl]Azetidine Hydrochloric Acid Salt (+)-Enantiomer of

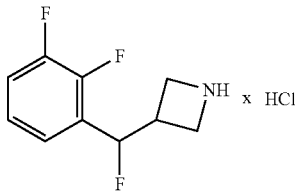 [SMILES: Fc1cccc(C(F)C2CNC2)c1F ; Cl]

(+)-Tert-butyl 3-[(2,3-difluorophenyl)(fluoro)methyl]azetidine-1-carboxylate (E2) (1.00 g, 3.32 mmol) was dissolved in methylene chloride (25 ml) and trifluoroacetic acid (3 ml) was added where after the mixture was stirred at ambient temperature for 15 h. The solvent was evaporated and the crude product was added to a SCX-3 SPE-column, washed with Methanol and extracted with Methanol/TEA in a 4:1 ratio. The solvents were evaporated and the crude product (0.5 g, 2.48 mmol) was dissolved in 5 ml Ethanol and hydrochloride acid in Ethanol (1.25 M, 2.0 ml) was added. The solvent was evaporated and the crude salt (title compound) was recrystallized from 2-propanol: M.p. 153-154° C. (HCl). MS m/z (relative intensity, 70 eV) 201 (M+, 3), 171 (43), 153 (bp), 151 (44), 145 (38). $^1$H NMR (800 MHz, MeOD) δ ppm 3.45-3.58 (m, 1 H) 4.07-4.16 (m, 2 H) 4.11 (dd, J=11.25, 4.89 Hz, 1 H) 4.16-4.22 (m, 2 H) 5.97-6.11 (m, 1 H) 7.26 (d, J=3.42 Hz, 2 H) 7.33 (td, J=10.27, 7.34 Hz, 1 H). $[\alpha]_D$=+18.4° (measured on the base with conc. 10 mg/ml).

Example 3

(−)-3-[(3,5-Difluorophenyl)(Fluoro)Methyl]Azetidine Fumarate Salt (−)-Enantiomer of

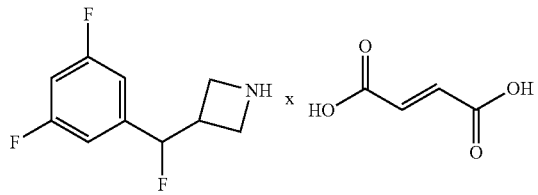 [SMILES: Fc1cc(F)cc(C(F)C2CNC2)c1 ; O=C(O)/C=C/C(=O)O]

Tert-butyl 3-[(3,5-difluorophenyl)(fluoro)methyl]azetidine-1-carboxylate (E1) (0.38, 1.26 mmol) was dissolved in methylene chloride (25 ml) and trifluoroacetic acid (3 ml) was added where after the mixture was stirred at ambient temperature for 15 h. The solvent was evaporated and the crude product was added to a SCX-3 SPE-column, washed with Methanol and extracted with Methanol/TEA in a 4:1 ratio. The solvents were evaporated and the crude product (0.20 g, 1.0 mmol) was dissolved in 5 ml Ethanol and fumaric acid (0.11 g, 1.0 mmol) was added.

Solvent was evaporated and the crude salt (title compound) was recrystallized from Methanol/diethyl ether: M.p. 146-147° C. (Fumarate). MS m/z (relative intensity, 70 eV) 201 (M+, 3), 171 (64), 153 (bp), 151 (63), 145 (43). $^1$H NMR (800 MHz, MeOD) δ ppm 3.41-3.52 (m, 1 H) 4.04 (t, J=10.03 Hz, 1 H) 4.11 (dd, J=13.20, 7.34 Hz, 2 H) 4.17 (t, J=10.03 Hz, 1 H) 5.72-5.86 (m, 1 H) 6.67* (s, 1.5 H) 6.92-6.99 (m, 1 H) 6.99-7.05 (m, 2 H). [α]$_D$=−34.4° (measured on the base with conc. 10 mg/ml).

Example 4

(+)-3-[(3,5-Difluorophenyl)(Fluoro)Methyl]Azetidine Fumarate Salt (+)-Enantiomer of

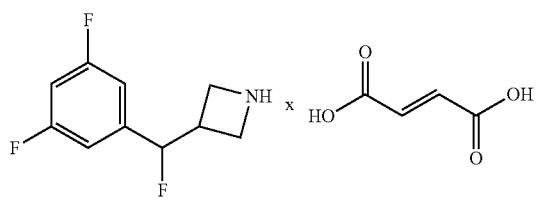 [SMILES: Fc1cc(F)cc(C(F)C2CNC2)c1 ; O=C(O)/C=C/C(=O)O]

Tert-butyl 3-[(3,5-difluorophenyl)(fluoro)methyl]azetidine-1-carboxylate (E2) (0.41 g, 1.36 mmol) was dissolved in methylene chloride (25 ml) and trifluoroacetic acid (3 ml) was added where after the mixture was stirred at ambient temperature for 15 h. The solvent was evaporated and the crude product was added to a SCX-3 SPE-column, washed with Methanol and extracted with Methanol/TEA in a 4:1 ratio. The solvents were evaporated and the crude product (0.25 g, 1.24 mmol) was dissolved in 5 ml Ethanol and fumaric acid (0.16 g, 1.24 mmol) was added. The solvent was evaporated and the crude salt (title compound) was recrystallized from Methanol/diethyl ether: M.p. 155-156° C. (Fumarate). MS m/z (relative intensity, 70 eV) 201 (M+, 3), 171 (64), 153 (bp), 151 (63), 145 (43). $^1$H NMR (800 MHz, MeOD) δ ppm 3.41-3.52 (m, 1 H) 4.04 (t, J=9.78 Hz, 1 H) 4.11 (dd, J=16.14, 7.34 Hz, 2 H) 4.17 (t, J=10.03 Hz, 1 H) 5.71-5.86 (m, 1 H) 6.67* (s, 1.5 H) 6.94-6.98 (m, 1 H) 7.00-7.04 (m, 2 H). [α]$_D$=+28.5° (measured on the base with conc. 10 mg/ml).

Example 5

3-[(3,4-Difluorophenyl)(Fluoro)Methyl]Azetidine Hydrochloric Acid Salt

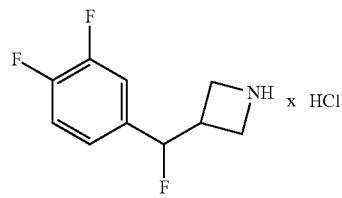 [SMILES: Fc1ccc(C(F)C2CNC2)cc1F ; Cl]

Tert-butyl 3-[(3,4-difluorophenyl)(fluoro)methyl]azetidine-1-carboxylate (0.66, 2.22 mmol) was dissolved in methylene chloride (25 ml) and trifluoroacetic acid (5 ml) was added where after the mixture was stirred at ambient temperature for 15 h. The solvent was evaporated and the crude product was added to a SCX-3 SPE-column, washed with Methanol and extracted with Methanol/TEA in a 4:1 ratio. The solvents were evaporated and the crude product (0.41 g, 2.03 mmol) was dissolved in 5 ml Ethanol and hydrochloric acid in Ethanol (1.25 M, 3.1 ml) was added. The solvent was evaporated and the crude salt (title compound) was recrystallized from Methanol/diethyl ether: M.p. 109-110° C. (HCl). MS m/z (relative intensity, 70 eV) 201 (M+, 2), 171 (42), 153 (bp), 151 (36), 145 (36). $^1$H NMR (800 MHz, MeOD) δ ppm 3.47 (dddd, J=18.65, 16.57, 9.05, 4.65 Hz, 1 H) 4.06-4.11 (m, 2 H) 4.11-4.19 (m, 2 H) 5.70-5.88 (m, 1 H) 7.21 (d, J=7.82 Hz, 1 H) 7.28-7.39 (m, 2 H).

Example 6

3-[(2,5-Difluorophenyl)(Fluoro)Methyl]Azetidine Oxalate Salt

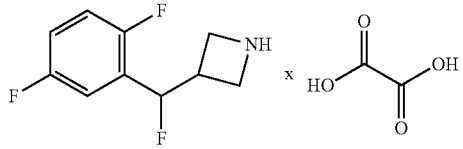 [SMILES: Fc1ccc(F)c(C(F)C2CNC2)c1 ; O=C(O)C(=O)O]

3-[(2,5-difluorophenyl)(fluoro)methyl]-1-(diphenylmethyl)azetidine (1.2 g, 3.27 mmol) was dissolved in methylene chloride (15 ml) and cooled to 0° C. 1-Chloroethyl chloroformate (0.7 g, 4.9 mmol)) was added where after the mixture was stirred at 0° C. for 18 h. The solvent was evaporated and the crude product was re-dissolved in methanol (20 ml) and stirred at ambient temperature for 3 hours. The methanol solution was added to a SCX-3 SPE-column, washed with methanol and extracted with methanol/triethylamine in a 4:1 ratio. The solvents were evaporated and the crude product (0.77 g) was further purified by flash column chromatography on silica gel (ethyl acetate:methanol, 1:0 to 1:1) to give the title compound (0.28 g, 1.38 mmol). The title compound was dissolved in 5 ml ethanol and oxalic acid dihydrate (0.17 g, 1.38 mmol) dissolved in ethanol (5 ml) was added and the mixture was evaporated to dryness and the crude salt (title compound) was re-crystallized from methanol/diethyl ether: M.p. 149° C. (oxalate). MS m/z (relative intensity, 70 eV) 201 (M+, 2), 171 (54), 153 (bp), 151 (46), 145 (48). 1H NMR (800 MHz, DMSO-d6) δ ppm 3.43 (m, 1 H), 3.82 (m, 1 H) 4.01-4.09 (m, 3 H), 6.03-6.1 (m, 1 H), 7.31-7.38 (m, 3 H).

Example 7

3-[(2,6-Difluorophenyl)(Fluoro)Methyl]Azetidine Oxalate Salt

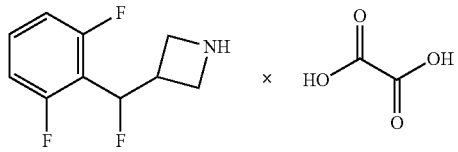 [SMILES: Fc1cccc(F)c1C(F)C1CNC1 ; O=C(O)C(=O)O]

Tert-butyl-3-[(2,6-difluorophenyl)(fluoro)methyl]azetidine-1-carboxylate (1.2 g, 3.98 mmol) was dissolved in methylene chloride (15 ml) and trifluoroacetic acid (6 ml, 78 mmol) was added and the mixture was stirred at ambient temperature for 1 hour. The mixture was then evaporated and the crude product was added to a SCX-3 SPE-column, washed with methanol and extracted with methanol/triethylamine in a 4:1 ratio. The solvents were evaporated and the crude product (0.82 g) was further purified by flash column chromatography on silica gel (ethyl acetate:methanol, 1:0 to 1:1) to give the title compound (0.74 g, 3.66 mmol). The title compound was dissolved in 5 ml ethanol and oxalic acid dihydrate (0.46 g, 3.66 mmol) dissolved in ethanol (5 ml) was added and the mixture was evaporated to dryness and the crude salt (title compound) was re-crystallized from methanol/diethyl ether: M.p. 169.4° C. (oxalate). MS m/z (relative intensity, 70 eV) 201 (M+, 2), 171 (42), 153 (bp), 151 (31), 145 (48). 1H NMR (800 MHz, CD3OD) δ ppm 3.6 (m, 1 H), 3.99 (m, 1 H) 4.17 (m, 1 H), 4.26 (m, 1 H), 4.34 (m, 1 H), 4.5 (m, 1 H), 6.06-6.22 (dd, 1 H), 7.05 (m, 2H), 7.48 (m, 1 H).

Example 8

3-[(2,4-Difluorophenyl)(Fluoro)Methyl]Azetidine Oxalate Salt

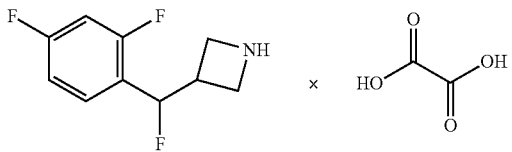 [SMILES: Fc1ccc(C(F)C2CNC2)c(F)c1 ; O=C(O)C(=O)O]

Tert-butyl-3-[(2,4-difluorophenyl)(fluoro)methyl]azetidine-1-carboxylate (0.54 g, 1.79 mmol) was dissolved in methylene chloride (10 ml) and trifluoroacetic acid (4 ml, 52 mmol) was added and the mixture was stirred at ambient temperature for 1 hour. The mixture was then evaporated and the crude product was added to a SCX-3 SPE-column, washed with methanol and extracted with methanol/triethylamine in a 4:1 ratio. The solvents were evaporated and the crude product (0.34 g, 1.71 mmol) was dissolved in 5 ml ethanol and oxalic acid dihydrate (0.216 g, 1.71 mmol) dissolved in Ethanol (5 ml) was added and the mixture was evaporated to dryness and the crude salt (title compound) was re-crystallized from methanol/diethyl ether: M.p. 152.5° C. (oxalate). MS m/z (relative intensity, 70 eV) 201 (M+, 1), 171 (41), 153 (bp), 151 (34), 145 (47). 1H NMR (800 MHz, CD3OD) δ ppm 3.5 (m, 1 H), 4.06 (m, 1 H), 4.13 (m, 1 H), 4.19 (m, 2 H), 5.94/5.99 (dd, 1 H), 7.03 (m, 2H), 7.48 (m, 1 H).

Example 9

3-[Fluoro(2,3,5-Trifluorophenyl)Methyl]Azetidine Oxalate Salt

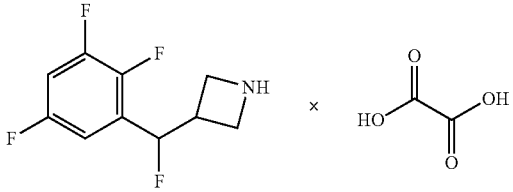 [SMILES: Fc1cc(F)c(F)c(C(F)C2CNC2)c1 ; O=C(O)C(=O)O]

Tert-butyl-3-[fluoro(2,3,5-trifluorophenyl)methyl]azetidine-1-carboxylate (1.62 g, 5.09 mmol) was dissolved in methylene chloride (20 ml) and trifluoroacetic acid (6 ml, 78 mmol) was added and the mixture was stirred at ambient temperature for 1 hour. The mixture was then evaporated and the crude product was re-dissolved in 10% $Na_2CO_3$ and the aqueous phase was extracted with ethyl acetate and the pooled organic phase was dried ($Na_2SO_4$), filtered and evaporated (yield 1.09 g, 5.0 mmol). The crude product was dissolved in 5 ml ethanol and oxalic acid dihydrate (0.63 g, 5.0 mmol) dissolved in ethanol (5 ml) was added and the mixture was evaporated to dryness and the crude salt (title compound) was re-crystallized from methanol/diethyl ether: M.p. 138.2° C. (oxalate). MS m/z (relative intensity, 70 eV) 219 (M+, 5), 189 (33), 171 (bp), 169 (40), 163 (43). 1H NMR (800 MHz, CD3OD) δ ppm 3.5 (m, 1 H), 4.1 (m, 2 H), 4.2 (m, 2 H), 6.01/6.07 (dd, 1 H), 7.09 (m, 1H), 7.23 (m, 1 H).

Example 10

3-[Fluoro(2,4,6-Trifluorophenyl)Methyl]Azetidine Oxalate Salt

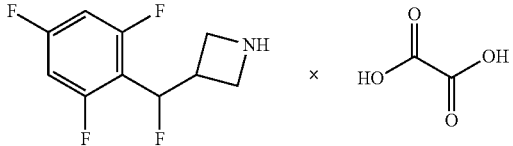 [SMILES: Fc1cc(F)c(C(F)C2CNC2)c(F)c1 ; O=C(O)C(=O)O]

Tert-butyl-3-[fluoro(2,4,6-trifluorophenyl)methyl]azetidine-1-carboxylate (0.995 g, 3.12 mmol) was dissolved in methylene chloride (10 ml) and trifluoroacetic acid (4 ml, 52 mmol) was added and the mixture was stirred at ambient temperature for 1 hour. The mixture was then evaporated and the crude product was re-dissolved in 10% $Na_2CO_3$ and the aqueous phase was extracted with ethyl acetate and the pooled organic phase was dried ($Na_2SO_4$), filtered and evaporated (yield 0.67 g, 3.06 mmol). The crude product was dissolved in 5 ml ethanol and oxalic acid dihydrate (0.385 g, 3.06 mmol) dissolved in ethanol (5 ml) was added and the mixture was evaporated to dryness and the crude salt (title compound) was re-crystallized from methanol/diethyl ether: M.p. 149.6° C. (oxalate). MS m/z (relative intensity, 70 eV) 219 (M+, 2), 171 (bp), 169 (24), 163 (56), 145 (25). 1H NMR (800 MHz, DMSO-d6) δ ppm 3.5 (m, 1 H), 3.7 (m, 1 H), 4.01 (m, 1 H), 4.13 (m, 2 H), 6.12/6.17 (dd, 1 H), 7.31 (m, 2H).

Example 11

3-[Fluoro(2,3,4-Trifluorophenyl)Methyl]Azetidine Oxalate Salt

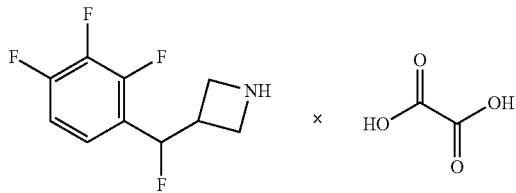 [SMILES: Fc1ccc(C(F)C2CNC2)c(F)c1F ; O=C(O)C(=O)O]

Tert-butyl-3-[fluoro(2,3,4-trifluorophenyl)methyl]azetidine-1-carboxylate (1.2 g, 3.77 mmol) was dissolved in methylene chloride (10 ml) and trifluoroacetic acid (4 ml, 52 mmol) was added and the mixture was stirred at ambient temperature for 1 hour. The mixture was then evaporated and the crude product was re-dissolved in 10% $Na_2CO_3$ and the aqueous phase was extracted with methyl tert-butyl ether and the pooled organic phase was dried ($Na_2SO_4$), filtered and evaporated (0.67 g, 3.06 mmol). The crude product was dissolved in 5 ml Ethanol and oxalic acid dihydrate (0.385 g, 3.06 mmol) dissolved in ethanol (5 ml) was added and the mixture was evaporated to dryness and the crude salt (title compound) was re-crystallized from methanol/diethyl ether: M.p. 157.7° C. (oxalate). MS m/z (relative intensity, 70 eV) 219 (M+, 3), 189 (27), 171 (bp), 169 (29), 163 (41). 1H NMR (800 MHz, CD3OD) δ ppm 3.5 (m, 1 H), 4.07 (m, 1 H), 4.14 (m, 1 H), 4.20 (m, 2 H), 5.96/6.12 (dd, 1 H), 7.20 (m, 1H), 7.26 (m, 1H).

Example 12

3-[Fluoro(3,4,5-Trifluorophenyl)Methyl]Azetidine Oxalate Salt

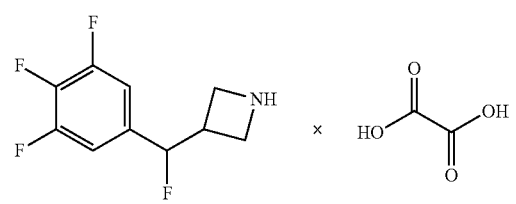 [SMILES: Fc1cc(C(F)C2CNC2)cc(F)c1F ; O=C(O)C(=O)O]

Tert-butyl-3-[fluoro(3,4,5-trifluorophenyl)methyl]azetidine-1-carboxylate (1.2 g, 3.77 mmol) was dissolved in methylene chloride (10 ml) and trifluoroacetic acid (4 ml, 52 mmol) was added and the mixture was stirred at ambient temperature for 1 hour. The mixture was then evaporated and the crude product was re-dissolved in 10% $Na_2CO_3$ and the aqueous phase was extracted with methyl tert-butyl ether and the pooled organic phase was dried ($Na_2SO_4$), filtered and evaporated (yield 0.64 g, 2.92 mmol). The crude product was dissolved in 5 ml ethanol and oxalic acid dihydrate (0.37 g, 2.92 mmol) dissolved in ethanol (5 ml) was added and the mixture was evaporated to dryness and the crude salt (title compound) was re-crystallized from methanol/diethyl ether: M.p. 123.2° C. (oxalate). MS m/z (relative intensity, 70 eV) 219 (M+, 2), 189 (24), 171 (bp), 169 (30), 163 (34). 1H NMR (800 MHz, CD3OD) δ ppm 3.45 (m, 1 H), 4.04-4.13 (m, 3 H), 4.17 (m, 1 H), 5.73/5.78 (dd, 1 H), 7.20 (t, 2H).

Example 13

3-[(3,5-Difluorophenyl)(Fluoro)Methyl]Azetidine

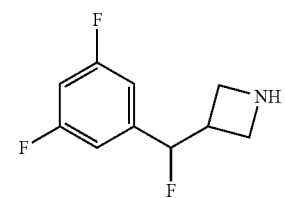 [SMILES: Fc1cc(F)cc(C(F)C2CNC2)c1]

Tert-butyl-3-[(3,5-difluorophenyl)(fluoro)methyl]azetidine-1-carboxylate (1.0 g, 3.32 mmol) was dissolved in methylene chloride (10 ml) and trifluoroacetic acid (4 ml, 52 mmol) was added and the mixture was stirred at ambient temperature for 1 hour. The mixture was then evaporated and the crude product was re-dissolved in 10% $Na_2CO_3$ and the aqueous phase was extracted with ethyl acetate and the pooled organic phase was dried ($Na_2SO_4$), filtered and evaporated (0.54 g, 2.69 mmol). MS m/z (relative intensity, 70 eV) 201 (M+, 2), 171 (63), 153 (bp), 151 (52), 145 (40).

Example 14

3-[(2,3-Difluorophenyl)(Fluoro)Methyl]Azetidine

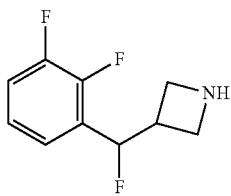 [SMILES: Fc1cccc(C(F)C2CNC2)c1F]

Tert-butyl-3-[(2,3-difluorophenyl)(fluoro)methyl]azetidine-1-carboxylate (1.0 g, 3.32 mmol) was dissolved in methylene chloride (10 ml) and trifluoroacetic acid (4 ml, 52 mmol) was added and the mixture was stirred at ambient temperature for 1 hour. The mixture was then evaporated and the crude product was re-dissolved in 10% $Na_2CO_3$ and the aqueous phase was extracted with ethyl acetate and the pooled organic phase was dried ($Na_2SO_4$), filtered and evaporated (660 mg, 3.3 mmol). MS m/z (relative intensity, 70 eV) 201 (M+, 2), 171 (41), 153 (bp), 151 (42), 145 (39).

Example 15

3-[(2,3-Difluorophenyl)(Fluoro)Methyl]-1-Methyl-azetidine

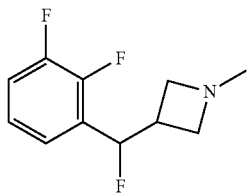

3-[2,3-Difluorophenyl)(fluoro)methyl]azetidine (90 mg, 0.45 mmol) was dissolved in acetonitrile (4 ml) and paraformaldehyde (37% aq, 0.17 ml, 2.23 mmol) was added. The mixture was stirred at ambient temperature for 5 min then sodium cyanoborohydride (56 mg, 0.89 mmol) was added in small portions to the mixture. The final mixture was stirred at ambient temperature for 2 hours and then water and saturated NaHCO3 aq solution was added and extracted with ethyl acetate. The pooled organic phase was dried (Na2CO3), filtered and evaporated to dryness (5.1 mg). MS m/z (relative intensity, 70 eV) 215 (M+, bp), 171 (62), 151 (82), 145 (81), 57 (49).). 1H NMR (800 MHz, CDCl3) δ ppm 2.36 (s, 3H), 3.0 (m, 1 H), 3.1 (t, 1 H), 3.3 (t, 1 H) 3.43 (m, 2 H), 5.82/5.88 (dd, 1 H), 7.13 (m, 3H)

Example 16

3-[(2,3-Difluorophenyl)(Fluoro)Methyl]-1-Ethylazetidine Hydrochloric Acid Salt

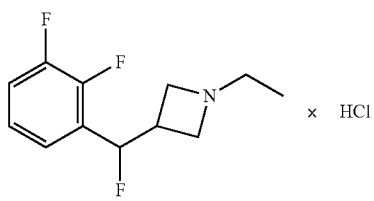 [SMILES: CCN1CC(C(F)c2cccc(F)c2F)C1 ; Cl]

3-[2,3-Difluorophenyl)(fluoro)methyl]azetidine (250 mg, 1.24 mmol) was dissolved in tetrahydrofuran (15 ml) and NEt3 (0.52 ml, 3.73 mmol) and iodoethane (0.15 ml, 1.86 mmol) was added. The mixture was stirred at ambient temperature for 24 hours then evaporated to dryness. The crude residue was re-dissolved in 10% aq HCl solution and extracted with methyl tert-butyl ether. The water phase was then basified with 10% aq Na2CO3 solution and extracted with methyl tert-butyl ether. The pooled organic phase was dried (Na2SO4), filtered and evaporated to dryness. The crude product was further purified by flash column chromatography on silica gel (ethyl acetate:methanol, 100:0 to 70:30) to give the title compound (165 mg, 0.72 mmol). The crude product was dissolved in 5 ml ethanol and hydrochloric acid in ethanol (1.25 M, 5 ml) was added. The solvent was evaporated and the crude salt (title compound) was recrystallized from methanol/diethyl ether: M.p. 130.8° C. (HCl). MS m/z (relative intensity, 70 eV) 229 (M+, 35), 214 (bp), 151 (29), 145 (56), 57 (67). 1H NMR (800 MHz, CD3OD) δ ppm 1.24 (t, 3H), 3.33 (m, 3H), 3.53 (m, 1 H), 4.03-4.44 (m, 3 H), 6.09 (m, 1 H), 7.3 (m, 2H), 7.36 (m, 1H)

Example 17

3-[(2,3-Difluorophenyl)(Fluoro)Methyl]-1-Propylazetidine Oxalate Salt

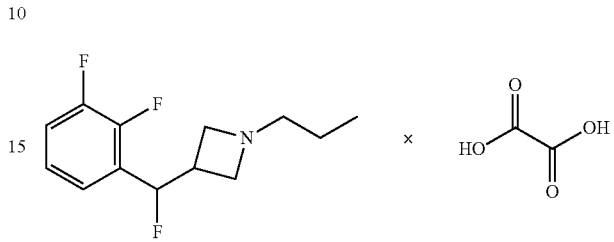

3-[2,3-Difluorophenyl)(fluoro)methyl]azetidine (200 mg, 0.99 mmol) was dissolved in tetrahydrofuran (8 ml) and NEt3 (0.42 ml, 2.98 mmol) and 1-iodopropane (0.14 ml, 1.49 mmol) was added. The mixture was stirred at ambient temperature for 24 hours then evaporated to dryness. The crude residue was re-dissolved in 10% aq HCl solution and extracted with methyl tert-butyl ether. The water phase was then basified with 10% aq Na2CO3 solution and extracted with methyl tert-butyl ether. The pooled organic phase was dried (Na2SO4), filtered and evaporated to dryness. The crude product was further purified by flash column chromatography on silica gel (ethyl acetate:methanol, 100:0 to 85:15) to give the title compound (101 mg, 0.41 mmol). The purified product was dissolved in 5 ml Ethanol and oxalic acid dihydrate (52.4 mg, 0.41 mmol) dissolved in ethanol (5 ml) was added and the mixture was evaporated to dryness and the crude salt (title compound) was re-crystallized from methanol/diethyl ether: M.p. 137.4° C. (oxalate) MS m/z (relative intensity, 70 eV) 243 (M+, 8), 215 (14), 214 (bp), 153 (11), 145 (25). 1H NMR (800 MHz, DMSO-d6) δ ppm 0.86 (t, 3H), 1.47 (m, 2H), 3.03 (t, 2 H), 3.41 (m, 1 H), 3.83 (t, 1H), 4.04-4.15 (m, 3 H), 6.09/6.15 (dd, 1 H), 7.29 (m, 2H), 7.51 (m, 1H)

Example 18

3-[(3,5-Difluorophenyl)(Fluoro)Methyl]-1-Methyl-azetidine

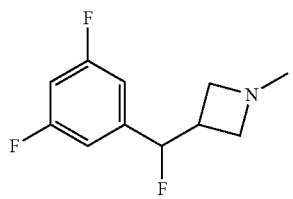

3-[3,5-Difluorophenyl)(fluoro)methyl]azetidine (100 mg, 0.5 mmol) was dissolved in acetonitrile (4.5 ml) and paraformaldehyde (37% aq, 0.19 ml, 2.48 mmol) was added. The mixture was stirred at ambient temperature for 5 min then sodium cyanoborohydride (62 mg, 0.99 mmol) was added in small portions to the mixture. The final mixture was stirred at ambient temperature for 2 hours and then water and saturated NaHCO3 aq solution was added and extracted with ethyl acetate. The pooled organic phase was dried (Na₂SO₄), filtered and evaporated to dryness. The crude product was further purified by flash column chromatography on silica gel (ethyl acetate:methanol, 100:0 to 75:25) to give the title compound (5 mg, 0.023 mmol) MS m/z (relative intensity, 70 eV) 215 (M+, 76), 171 (67), 151 (bp), 145 (82), 57 (76).

Example 19

3-[(3,5-Difluorophenyl)(Fluoro)Methyl]-1-Ethylazetidine Oxalate Salt

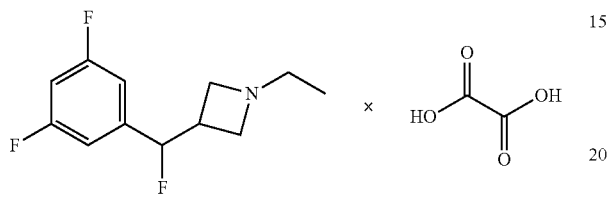

3-[3,5-Difluorophenyl)(fluoro)methyl]azetidine (285 mg, 1.42 mmol) was dissolved in tetrahydrofuran (8 ml) and NEt₃ (0.59 ml, 4.25 mmol) and iodoethane (0.17 ml, 2.12 mmol) was added. The mixture was stirred at ambient temperature for 20 hours then evaporated to dryness. The crude residue was re-dissolved in 10% HCl solution and extracted with methyl tert-butyl ether. The water phase was then basified with 10% aq Na₂CO₃ solution and extracted with methyl tert-butyl ether. The pooled organic phase was dried (Na₂SO₄), filtered and evaporated to dryness. The crude product was further purified by flash column chromatography on silica gel (ethyl acetate:methanol, 100:0 to 70:30) to give the title compound (yield 117 mg, 0.51 mmol). The purified product was dissolved in 5 ml ethanol and oxalic acid dihydrate (64 mg, 0.51 mmol) dissolved in ethanol (5 ml) was added and the mixture was evaporated to dryness and the crude salt (title compound) was re-crystallized from methanol/diethyl ether: M.p. 137.3° C. (oxalate). MS m/z (relative intensity, 70 eV) 229 (M+, 44), 214 (bp), 151 (39), 145 (54), 57 (87). 1H NMR (800 MHz, DMSO-d6) δ ppm 1.05 (t, 3H), 3.09 (m, 2H), 3.33 (m, 1 H), 3.89 (m, 1H), 4.0-4.06 (m, 3 H), 5.85/5.91 (dd, 1 H), 7.17 (m, 2H), 7.28 (m, 1H)

Example 20

3-[(3,5-Difluorophenyl)(Fluoro)Methyl]-1-Propylazetidine Oxalate Salt

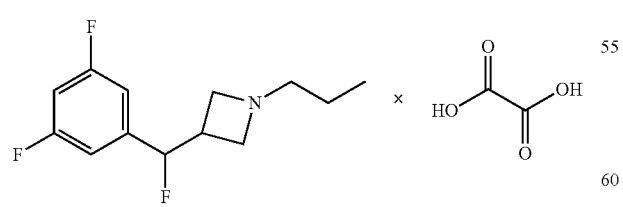

3-[3,5-Difluorophenyl)(fluoro)methyl]azetidine (150 mg, 0.74 mmol) was dissolved in tetrahydrofuran (8 ml) and NEt3 (0.31 ml, 2.23 mmol) and 1-iodopropane (0.11 ml, 1.11 mmol) was added. The mixture was stirred at ambient temperature for 24 hours then evaporated to dryness. The crude residue was re-dissolved in 10% aq HCl solution and extracted with methyl tert-butyl ether. The water phase was then basified with 10% aq Na₂CO₃ solution and extracted with methyl tert-butyl ether. The pooled organic phase was dried (Na₂SO₄), filtered and evaporated to dryness. The crude product was further purified by flash column chromatography on silica gel (ethyl acetate:methanol, 100:0 to 95:5) to give the title compound (yield 85 mg, 0.35 mmol). The purified product (80 mg) was dissolved in 5 ml ethanol and oxalic acid dihydrate (41.5 mg, 0.329 mmol) dissolved in ethanol (5 ml) was added and the mixture was evaporated to dryness and the crude salt (title compound) was re-crystallized from methanol/diethyl ether: M.p. 156.9° C. (oxalate). MS m/z (relative intensity, 70 eV) 243 (M+, 8), 215 (14), 214 (bp), 145 (22), 70 (11). 1H NMR (800 MHz, DMSO-d6) δ ppm 0.87 (t, 3H), 1.47 (m, 2H), 3.0 (t, 2 H), 3.3 (m, 1 H), 3.9 (t, 1H), 4.01-4.06 (m, 3 H), 5.84/5.90 (dd, 1H), 7.17 (m, 2H), 7.28 (m, 1H)

Example 21

3-[FLUORO(2,3,5-Trifluorophenyl)Methyl]-1-Methylazetidine

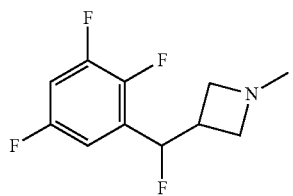 [SMILES: CN1CC(C(F)c2cc(F)cc(F)c2F)C1]

3-[2,3,5-Trifluorophenyl)(fluoro)methyl]azetidine (135 mg, 0.61 mmol) was dissolved in acetonitrile (6 ml) and paraformaldehyde (37% aq, 0.23 ml, 3.08 mmol) was added. The mixture was stirred at ambient temperature for 5 min then sodium cyanoborohydride (77.4 mg, 1.23 mmol) was added in small portions to the mixture. The final mixture was stirred at ambient temperature for 2 hours and then water and saturated NaHCO₃ aq solution was added and extracted with ethyl acetate. The pooled organic phase was dried (Na₂SO₄), filtered and evaporated to dryness. The crude product was further purified by flash column chromatography on silica gel (ethyl acetate:methanol, 100:0 to 90:10) to give the title compound (0.74 g, 3.66 mmol). MS m/z (relative intensity, 70 eV) 233 (M+, bp), 171 (44), 169 (67), 163 (76), 57 (56). 1H NMR (800 MHz, CDCl3) δ ppm 2.35 (s, 3H), 2.95 (m, 1H), 3.10 (t, 1 H), 3.26 (t, 1 H), 3.40 (m, 2H), 5.81/5.87 (dd, 1 H), 6.87-6.93 (m, 2H).

Example 22

1-Ethyl-3-[Fluoro(2,3,5-Trifluorophenyl)Methyl] Azetidine Oxalate Salt

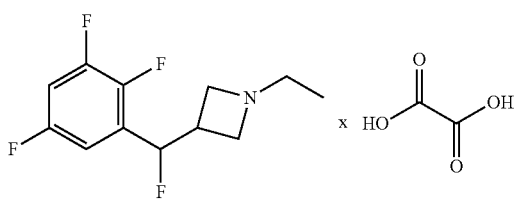

3-[2,3,5-Trifluorophenyl)(fluoro)methyl]azetidine (250 mg, 1.14 mmol) was dissolved in tetrahydrofuran (8 ml) and NEt3 (0.48 ml, 3.42 mmol) and iodoethane (0.14 ml, 1.71 mmol) was added. The mixture was stirred at ambient temperature for 20 hours then evaporated to dryness. The crude residue was re-dissolved in 10% HCl solution and extracted with methyl tert-butyl ether. The water phase was then basified with 10% aq $Na_2CO_3$ solution and extracted with methyl tert-butyl ether. The pooled organic phase was dried ($Na_2SO_4$), filtered and evaporated to dryness. The crude product was further purified by flash column chromatography on silica gel (ethyl acetate:methanol, 100:0 to 80:20) to give the title compound (77 mg, 0.31 mmol). The purified product (77 mg) was dissolved in 5 ml ethanol and oxalic acid dihydrate (39.3 mg, 0.31 mmol) dissolved in ethanol (5 ml) was added and the mixture was evaporated to dryness and the crude salt (title compound) was re-crystallized from methanol/diethyl ether: M.p. 127.1° C. (oxalate). MS m/z (relative intensity, 70 eV) 247 (M+, 26), 232 (87), 169 (29), 163 (61), 57 (bp). 1H NMR (800 MHz, DMSO-d6) δ ppm 1.06 (t, 3H), 3.10 (q, 2H), 3.39 (m, 1 H), 3.83 (m, 1 H), 4.04-4.10 (m, 3 H), 6.10/6.16 (dd, 1 H), 7.25 (m, 1H), 7.64 (m, 1H)

Example 23

3-[Fluoro(2,3,5-Trifluorophenyl)Methyl]-1-Propylazetidine Oxalate Salt

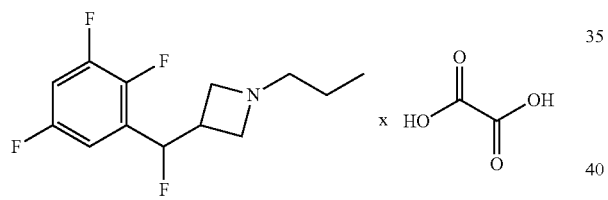

3-[2,3,5-Trifluorophenyl)(fluoro)methyl]azetidine (200 mg, 0.91 mmol) was dissolved in tetrahydrofuran (8 ml) and NEt3 (0.38 ml, 2.74 mmol) and 1-iodopropane (0.13 ml, 1.37 mmol) was added. The mixture was stirred at ambient temperature for 24 hours then evaporated to dryness. The crude residue was re-dissolved in 10% aq HCl solution and extracted with methyl tert-butyl ether. The water phase was then basified with 10% aq $Na_2CO_3$ solution and extracted with methyl tert-butyl ether. The pooled organic phase was dried ($Na_2SO_4$), filtered and evaporated to dryness. The crude product was further purified by flash column chromatography on silica gel (ethyl acetate:methanol, 100:0 to 95:5) to give the title compound (75 mg, 0.29 mmol). The purified product (75 mg) was dissolved in 5 ml ethanol and oxalic acid dihydrate (36.2 mg, 0.29 mmol) dissolved in Ethanol (5 ml) was added and the mixture was evaporated to dryness and the crude salt (title compound) was re-crystallized from methanol/diethyl ether: M.p. 159° C. (oxalate). MS m/z (relative intensity, 70 eV) 261 (M+, 7), 233 (14), 232 (bp), 163 (22), 70 (9). 1H NMR (800 MHz, DMSO-d6) δ ppm 0.87 (t, 3H), 1.47 (m, 2H), 3.02 (t, 2 H), 3.39 (m, 1 H), 3.83 (t, 1H), 4.05-4.13 (m, 3 H), 6.09/6.15 (dd, 1 H), 7.25 (m, 1H), 7.63 (m, 1H)

Example 24

1-Ethyl-3-[Fluoro(2,3,4-Trifluorophenyl)Methyl] Azetidine

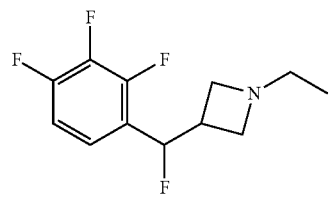 [SMILES: CCN1CC(C(F)c2ccc(F)c(F)c2F)C1]

3-[2,3,4-Trifluorophenyl)(fluoro)methyl]azetidine (300 mg, 1.37 mmol) was dissolved in 1,2-dichloroethane (10 ml) and acetaldehyde (0.090 ml, 1.64 mmol) and acetic acid (0.078 ml, 1.37 mmol) was added. The mixture was stirred at ambient temperature for 5 min then sodium triacetoxy borohydride (435 mg, 2.05 mmol) was added in small portions to the mixture. The final mixture was stirred at ambient temperature for 20 hours and then 10% $NaHCO_3$ aq solution was added and extracted with methylene chloride. The pooled organic phase was washed (brine), dried ($Na_2SO_4$), filtered and evaporated to dryness (0.33 g). The crude product was further purified by flash column chromatography on silica gel (ethyl acetate:methanol, 100:0 to 70:30) to give the title compound (144 mg). MS m/z (relative intensity, 70 eV) 247 (M+, 20), 232 (62), 163 (68), 71 (24), 57 (bp).

Example 25

3-[Fluoro(2,3,4-Trifluorophenyl)Methyl]-1-Propylazetidine

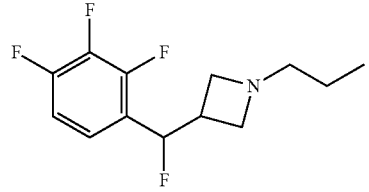 [SMILES: CCCN1CC(C(F)c2ccc(F)c(F)c2F)C1]

3-[2,3,4-Trifluorophenyl)(fluoro)methyl]azetidine (90 mg, 0.41 mmol) was dissolved in 1,2-dichloroethane (5 ml) and propionaldehyde (0.036 ml, 0.49 mmol) and acetic acid (0.024 ml, 0.41 mmol) was added. The mixture was stirred at ambient temperature for 5 min then sodium triacetoxy borohydride (130.5 mg, 0.62 mmol) was added in small portions to the mixture. The final mixture was stirred at ambient temperature for 20 hours and then 10% $NaHCO_3$ aq solution was added and extracted with methylene chloride. The pooled organic phase was washed (brine), dried (Na2SO4), filtered and evaporated to dryness (95 mg). MS m/z (relative intensity, 70 eV) 261 (M+, 54), 189 (18), 171 (bp), 169 (22), 163 (38).

Example 26

1-Ethyl-3-[Fluoro(3,4,5-Trifluorophenyl)Methyl] Azetidine Oxalate Salt

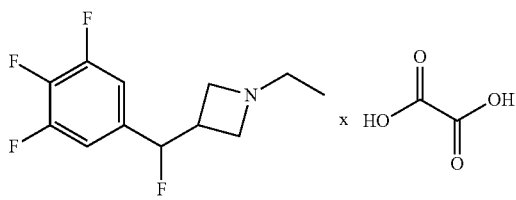

3-[3,4,5-Trifluorophenyl)(fluoro)methyl]azetidine (350 mg, 1.60 mmol) was dissolved in 1,2-dichloro ethane (15 ml) and acetaldehyde (0.105 ml, 1.92 mmol) and acetic acid (0.092 ml, 1.60 mmol) was added. The mixture was stirred at ambient temperature for 5 min then sodium triacetoxy borohydride (508 mg, 2.39 mmol) was added in small portions to the mixture. The final mixture was stirred at ambient temperature for 20 hours and then 10% $NaHCO_3$ aq solution was added and extracted with methylene chloride. The pooled organic phase was washed (brine), dried (Na2SO4), filtered and evaporated to dryness (350 mg). The crude product was further purified by flash column chromatography on silica gel (ethyl acetate:methanol, 100:0 to 75:25) to give the title compound (208 mg). The purified product (195 mg) was dissolved in 5 ml Ethanol and oxalic acid dihydrate (99.5 mg, 0.79 mmol) dissolved in ethanol (5 ml) was added and the mixture was evaporated to dryness and the crude salt (title compound) was re-crystallized from methanol/diethyl ether: M.p. 129.8° C. MS m/z (relative intensity, 70 eV) 247 (M+, 40), 232 (bp), 169 (29), 163 (58), 57 (82).

Example 27

3-[Fluoro(3,4,5-Trifluorophenyl)Methyl]-1-Propylazetidine

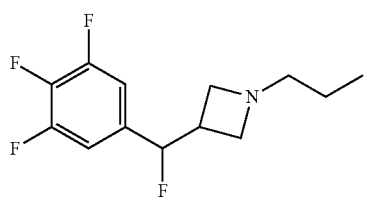 [SMILES: CCCN1CC(C(F)c2cc(F)c(F)c(F)c2)C1]

3-[3,4,5-Trifluorophenyl)(fluoro)methyl]azetidine (200 mg, 0.91 mmol) was dissolved in 1,2-dichloroethane (10 ml) and propionaldehyde (0.079 ml, 1.095 mmol) and acetic acid (0.052 ml, 0.91 mmol) was added. The mixture was stirred at ambient temperature for 5 min then sodium triacetoxy borohydride (290 mg, 1.36 mmol) was added in small portions to the mixture. The final mixture was stirred at ambient temperature for 20 hours and then 10% Na2CO3 aq solution was added and extracted with methylene chloride. The pooled organic phase was washed (brine), dried ($Na_2SO_4$), filtered and evaporated to dryness (193 mg). MS m/z (relative intensity, 70 eV) 261 (M+, 61), 189 (18), 171 (bp), 169 (22), 163 (31).

Example 28

3-[Fluoro(2,3,5,6-Tetrafluorophenyl)Methyl]Azetidine Oxalate Salt

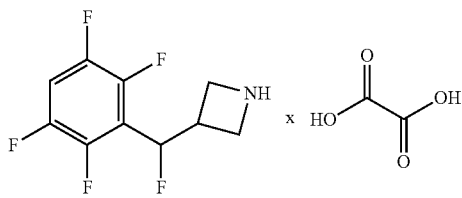

Tert-butyl-3-[(2,3,5,6-tetrafluorophenyl)(fluoro)methyl] azetidine-1-carboxylate (2.27 g, 6.73 mmol) was dissolved in methylene chloride (15 ml) and trifluoroacetic acid (4 ml, 52 mmol) was added and the mixture was stirred at ambient temperature for 1 hour. The mixture was then evaporated and the crude product was re-dissolved in 10% Na2CO3 and the aqueous phase was extracted with ethyl acetate and the pooled organic phase was dried ($Na_2SO_4$), filtered and evaporated (yield 1.36 g, 5.72 mmol). The crude product (555 mg, 2.34 mmol) was dissolved in 10 ml ethanol and oxalic acid dihydrate (295 mg, 2.34 mmol) dissolved in ethanol (5 ml) was added and the mixture was evaporated to dryness and the crude salt (title compound) was re-crystallized from warm methanol: M.p. 181.6° C. MS m/z (relative intensity, 70 eV) 237 (M+, 5), 217 (41), 189 (bp), 181 (49), 169 (46).

Example 29

3-[Fluoro(Pentafluorophenyl)Methyl]Azetidine

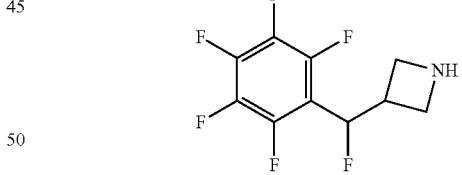

Tert-butyl-3-[(2,3,4,5,6-pentafluorophenyl)(fluoro) methyl]azetidine-1-carboxylate (3 g, 8.55 mmol) was dissolved in methylene chloride (20 ml) and trifluoroacetic acid (5 ml, 65 mmol) was added and the mixture was stirred at ambient temperature for 1 hour. The mixture was then evaporated and the crude product was re-dissolved in 10% $Na_2CO_3$ and the aqueous phase was extracted with ethyl acetate and the pooled organic phase was dried ($Na_2SO_4$), filtered and evaporated (yield 2.1 g). MS m/z (relative intensity, 70 eV) 255 (M+, 3), 208 (24), 207 (bp), 199 (52), 187 (35).

Example 30

3-[Fluoro(2,3,5,6-Tetrafluorophenyl)Methyl]-1-Methylazetidine

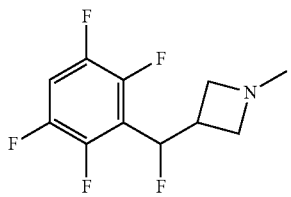 [SMILES: CN1CC(C(F)c2c(F)c(F)cc(F)c2F)C1]

3-[2,3,5,6-Tetrafluorophenyl)(fluoro)methyl]azetidine (85 mg, 0.36 mmol) was dissolved in methylene chloride (4 ml) and paraformaldehyde (37% aq, 0.08 ml, 1.07 mmol) and acetic acid (0.041 ml, 0.72 mmol) was added. The mixture was stirred at ambient temperature for 15 min then sodium triacetoxy borohydride (227.8 mg, 1.08 mmol) was added in one portion to the mixture. The final mixture was stirred at ambient temperature for 1 hour and then 10% $Na_2CO_3$ aq solution was added and extracted with methylene chloride. The pooled organic phase was washed with brine and dried ($Na_2SO_4$), filtered and evaporated to dryness (67 mg, 0.27 mmol). MS m/z (relative intensity, 70 eV) 251 (M+, bp), 187 (38), 181 (66), 169 (35), 57 (60).

Example 31

1-Ethyl-3-[Fluoro(2,3,5,6-Tetrafluorophenyl)Methyl]-Azetidine Oxalate SALT

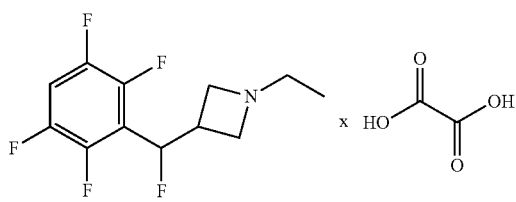

3-[2,3,5,6-Tetrafluorophenyl)(fluoro)methyl]azetidine (300 mg, 1.265 mmol) was dissolved in 1,2-dichloro ethane (10 ml) and acetaldehyde (0.09 ml, 1.65 mmol) and acetic acid (0.072 ml, 1.27 mmol) was added. The mixture was stirred at ambient temperature for 5 min then sodium triacetoxy borohydride (402 mg, 1.9 mmol) was added in small portions to the mixture. The final mixture was stirred at ambient temperature for 16 hours and then 10% $NaHCO_3$ aq solution was added and extracted with methylene chloride. The pooled organic phase was washed (brine), dried (Na2SO4), filtered and evaporated to dryness (306 mg). The crude product was further purified by flash column chromatography on silica gel (ethyl acetate:methanol, 100:0 to 80:20) to give the title compound (133 mg). The purified product (130 mg, 0.49 mmol) was dissolved in 5 ml Ethanol and oxalic acid dihydrate (61.8 mg, 0.49 mmol) dissolved in ethanol (5 ml) was added and the mixture was evaporated to dryness and the crude salt (title compound) was re-crystalized from methanol/diethyl ether: M.p. 145.9° C. MS m/z (relative intensity, 70 eV) 265 (M+, 30), 250 (bp), 181 (39), 163 (15), 57 (57)

Example 32

3-[Fluoro(2,3,5,6-Tetrafluorophenyl)Methyl]-1-Propylazetidine

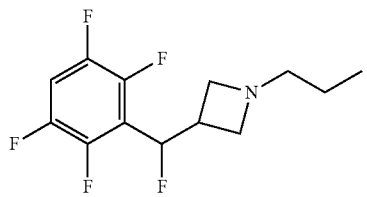 [SMILES: CCCN1CC(C(F)c2c(F)c(F)cc(F)c2F)C1]

3-[2,3,5,6-Tetrafluorophenyl)(fluoro)methyl]azetidine (200 mg, 0.84 mmol) was dissolved in 1,2-dichloro ethane (10 ml) and propionaldehyde (0.09 ml, 1.26 mmol) and acetic acid (0.048 ml, 0.84 mmol) was added. The mixture was stirred at ambient temperature for 5 min then sodium triacetoxy borohydride (321 mg, 1.52 mmol) was added in small portions to the mixture. The final mixture was stirred at ambient temperature for 16 hours and then 10% $NaHCO_3$ aq solution was added and extracted with methylene chloride. The pooled organic phase was washed (brine), dried ($Na_2SO_4$), filtered and evaporated to dryness (204 mg). MS m/z (relative intensity, 70 eV) 279 (M+, 94), 217 (27), 190 (29), 189 (bp), 181 (35)

Intermediates as described hereinafter were used in the Examples above. These inter-mediates may be prepared using the reactions described below, but other procedures and reactions may be used as well as appreciated by those skilled in the art.

Preparation 1

Tert-Butyl 3-[(2,3-Difluorophenyl)(Hydroxy)Methyl]Azetidine-1-Carboxylate

To a solution of 2,3-difluorobromobenzene (10.0 g, 51.8 mmol) in dry diethyl ether (120 ml), under nitrogen at −78° C., was added drop wise, n-hexyllithium (2.3 M in hexane, 22.5 ml, 51.8 mmol). The mixture was stirred for 10 min after which a solution of tert-butyl 3-formylazetidine-1-carboxylate (12.2 g, 49.2 mmol) in dry diethyl ether (30 ml) was added drop wise. The resulting mixture was stirred at −78° C. for 0.5 h and then brought to ambient temperature and stirred for 1 h. Water (50 ml) was added and the mixture was extracted with ethyl acetate (2×50 ml). The combined organic phase was washed with brine, dried (MgSO4), filtered and evaporated to dryness. The crude product was purified by flash column chromatography on silica gel (ethyl acetate/isooctane, 0:1 to 1:1) to give the title compound (6.55 g). MS m/z (rel. intensity, 70 eV) 299 (M+, 2), 244 (36), 225 (29), 153(99), 57 (bp).

Preparation 2

Tert-Butyl 3-[(2,3-Difluorophenyl)(Fluoro)Methyl]Azetidine-1-Carboxylate

Tert-butyl 3-[(2,3-difluorophenyl)(hydroxy)methyl]azetidine-1-carboxylate (5.54 g, 18.5 mmol) was dissolved in methylene chloride (100 ml) and cooled to −78° C. Deoxofluor (50%, 8.2 ml, 22.2 mmol) was added drop wise under 10 min and the resulting mixture was stirred at −78° C. for 0.5 h, warmed to ambient temperature and stirred for 3 h. Water (50 ml) was added and the organic phase was collected. The aqueous phase was extracted with methylene chloride (2×50 ml) and the pooled organic phase was dried (MgSO$_4$), filtered and evaporated. The crude product was purified by flash column chromatography on silica gel (ethyl acetate/isooctane, 0:1 to 1:2) to give the title compound (2.8 g, 9.2 mmol). MS m/z (rel. intensity, 70 eV) 301 (M+, 2), 246 (62), 153 (66), 145 (34), 57 (bp).

Preparation 3

(−)-Tert-Butyl 3-[(2,3-Difluorophenyl)(Fluoro)Methyl] Azetidine-1-Carboxylate

The enantiomers of tert-butyl 3-[(2,3-difluorophenyl)(fluoro)methyl]azetidine-1-carboxylate (2.8 g, 9.3 mmol) were separated by HPLC on Kromasil 10-Cellucoat (heptane/2-propanol/diethyl amine, 98:2:0.1). (−)-Enantiomer (1.0 g, 3.3 mmol). [α]D=−14.6° (methanol).

Preparation 4

(+)-Tert-Butyl 3-[(2,3-Difluorophenyl)(Fluoro)Methyl] Azetidine-1-Carboxylate

The enantiomers of tert-butyl 3-[(2,3-difluorophenyl)(fluoro)methyl]azetidine-1-carboxylate (2.8 g, 9.3 mmol) were separated by HPLC on Kromasil 10-Cellucoat (heptane/2-propanol/diethyl amine, 98:2:0.1). (+)-Enantiomer (1.3 g, 4.3 mmol). [α]D=+29.6° (methanol).

Preparation 5

Tert-Butyl 3-[(3,5-Difluorophenyl)(Hydroxy)Methyl]Azetidine-1-Carboxylate

To a solution of 3,5-difluorobromobenzene (2.0 g, 10.3 mmol) in dry tetrahydrofuran (50 ml), under nitrogen was added Mg (0.26 g, 10.8 mmol) and a corn of I$_2$ and the mixture was heated gently until exothermic reaction started. The mixture was stirred for 2 h after which a solution of tert-butyl 3-formylazetidine-1-carboxylate (1.8 g, 10.3 mmol) in dry diethyl ether (20 ml) was added drop wise. The resulting mixture was stirred for 0.5 h, saturated aqueous ammonium chloride (50 ml) was added and the organic phase was collected. The aqueous phase was extracted with ethyl acetate (2×50 ml). The combined organic phase was washed with brine, dried (MgSO$_4$), filtered and evaporated to dryness. The crude product was purified by flash column chromatography on silica gel (ethyl acetate/isooctane, 0:1 to 1:1) to give the title compound (1.92 g, 6.42 mmol). MS m/z (rel. intensity, 70 eV) 299 (M+, 2), 244 (34), 153(54), 127 (23), 57 (bp).

Preparation 6

Tert-Butyl 3-[(3,5-Difluorophenyl)(Fluoro)Methyl] Azetidine-1-Carboxylate

Tert-butyl 3-[(3,5-difluorophenyl)(hydroxy)methyl]azetidine-1-carboxylate (1.92 g, 6.42 mmol) was dissolved in methylene chloride (90 ml) and cooled to 0° C. Diethylaminosulfur trifluoride (1.72 ml, 13.02 mmol) dissolved in methylene chloride (10 ml) was added drop wise under 10 min and the resulting mixture was stirred at 0° C. for 0.5 h, warmed to ambient temperature and stirred for 0.5 h. Water (50 ml) was added and the organic phase was collected. The aqueous phase was extracted with methylene chloride (2×50 ml) and the pooled organic phase was dried (MgSO$_4$), filtered and evaporated. The crude product was purified by flash column chromatography on silica gel (ethyl acetate/isooctane, 0:1 to 1:3 to give the title compound (1.04 g, 3.45 mmol). MS m/z (rel. intensity, 70 eV) 301 (M+, 1), 246 (56), 165 (31), 153 (40), 57 (bp).

Preparation 7

Tert-Butyl 3-[(3,5-Difluorophenyl)(Fluoro)Methyl] Azetidine-1-Carboxylate, E1

The enantiomers of tert-butyl 3-[(3,5-difluorophenyl)(fluoro)methyl]azetidine-1-carboxylate (1.04 g, 3.45 mmol) were separated by HPLC on Kromasil 10-Cellucoat (heptane/2-propanol/diethyl amine, 98:2:0.1).

Preparation 8

Tert-Butyl 3-[(3,5-Difluorophenyl)(Fluoro)Methyl] Azetidine-1-Carboxylate, E2

The enantiomers of tert-butyl 3-[(3,5-difluorophenyl)(fluoro)methyl]azetidine-1-carboxylate (1.04 g, 3.45 mmol) were separated by HPLC on Kromasil 10-Cellucoat (heptane/2-propanol/diethyl amine, 98:2:0.1).

Preparation 9

Tert-Butyl 3-[(3,4-Difluorophenyl)(Hydroxy)Methyl]Azetidine-1-Carboxylate

To a solution of 3,4-difluorobromobenzene (4.0 g, 20.7 mmol) in dry diethyl ether (50 ml), under nitrogen was added Mg (0.50 g, 20.6 mmol) and a corn of I$_2$ and the mixture was heated gently until exothermic reaction started. The mixture was stirred for 15 min after which a solution of tert-butyl 3-formylazetidine-1-carboxylate (3.8 g, 20.5 mmol) in dry diethyl ether (20 ml) was added drop wise. The resulting mixture was stirred for 15 min, water (50 ml) was added and the organic phase was collected. The aqueous phase was extracted with methyl tertbutyl ether (2×50 ml). The combined organic phase was washed with brine, dried (MgSO$_4$), filtered and evaporated to dryness. The crude product was purified by flash column chromatography on silica gel (ethyl acetate/isooctane, 0:1 to 1:1) to give the title compound (4.1 g, 13.7 mmol). MS m/z (rel. intensity, 70 eV) 299 (M+, 1), 244 (24), 225 (27), 153 (72), 57 (bp).

Preparation 10

Tert-Butyl 3-[(3,4-Difluorophenyl)(Fluoro)Methyl] Azetidine-1-Carboxylate

Tert-butyl 3-[(3,4-difluorophenyl)(hydroxy)methyl]azetidine-1-carboxylate (4.1 g, 13.7 mmol) was dissolved in methylene chloride (120 ml) and cooled to 0° C. Diethylaminosulfur trifluoride (3.35 ml, 27.4 mmol) dissolved in methylene chloride (30 ml) was added drop wise under 10 min and the resulting mixture was stirred at 0° C. for 1 h, warmed to ambient temperature and stirred for 0.5 h. Water (50 ml) was added and the organic phase was collected. The aqueous phase was extracted with methylene chloride (2×50 ml) and the pooled organic phase was dried (MgSO$_4$), filtered and evaporated. The crude product was purified by flash column chromatography on silica gel (ethyl acetate/isooctane, 0:1 to 1:3 to give the title compound (1.04 g, 3.45 mmol). MS m/z (rel. intensity, 70 eV) 301 (M+, 2), 246 (49), 153 (54), 145 (30), 57 (bp).

Preparation 11

(2,5-Difluorophenyl)[1-(Diphenylmethyl)Azetidine-3-yl]Methanol

To a solution of isopropylmagnesium chloride lithium chloride complex in tetrahydrofuran (1.3 M, 12.5 ml, 16.3 mmol) was added 1-bromo-2,5-difluorobenzene (3 g, 15.5 mmol) dissolved in dry tetrahydrofuran (5 ml) and the mixture was stirred under nitrogen at ambient temperature for 1.5 hours. The reaction mixture was cooled to −10° C. and 1-(diphenylmethyl)azetidine-3-carbaldehyde (4.1 g, 16.3 mmol) dissolved in dry tetrahydrofuran (5 ml) was added in one portion and the temperature was raised to 0° C. and the mixture stirred for 20 min and then brought to ambient temperature and stirred for additional 30 min. The reaction mixture was quenched with saturated ammonium chloride solution and extracted with ethyl acetate. The pooled organic phase was washed with brine, dried ($Na_2SO_4$, filtered and evaporated to dryness. The crude product (4.76 g) was further purified by flash column chromatography on silica gel (ethyl acetate:methanol, 70:30) to give the title compound (1.56 g, 4.27 mmol). MS m/z (rel. intensity, 70 eV) 365 (M+, 15), 288 (72), 167 (bp), 165(34), 152 (20)

Preparation 12

3-[(2,5-Difluorophenyl)(Fluoro)Methyl]-1-(Diphenylmethyl)Azetidine (2,5-Difluorophenyl)[1-(diphenylmethyl)azetidine-3-yl]methanol (1.55 g, 4.24 mmol) was dissolved in dry methylene chloride (30 ml) and cooled to −78° C. under nitrogen.

Diethylaminosulfur trifluoride (DAST, 1.04 ml, 8.48 mmol) was added in one portion and the mixture stirred for 10 min and then brought to ambient temperature and stirred for additional 1 hour. The reaction mixture was quenched with saturated $NaHCO_3$ aq solution and extracted with methylene chloride. The pooled organic phase was washed with water, brine and dried ($Na_2SO_4$), filtered and finally evaporated to dryness. The crude product (1.66 g) was further purified by flash column chromatography on silica gel (ethyl acetate:methanol, 80:20) to give the title compound (1.22 g, 3.31 mmol). MS m/z (rel. intensity, 70 eV) 367 (M+, 21), 291 (20), 290 (bp), 167(84), 165 (34)

Preparation 13

Tert-Butyl 3-[(2,4-Difluorophenyl)(Hydroxy)Methyl]Azetidine-1-Carboxylate

To a solution of isopropylmagnesium chloride lithium chloride complex in tetrahydrofuran (1.3 M, 8.4 ml, 10.9 mmol) was added 1-bromo-2,4-difluorobenzene (2.0 g, 10.4 mmol) dissolved in dry tetrahydrofuran (5 ml) and the mixture was stirred under nitrogen at ambient temperature for 1 hour. The reaction mixture was cooled to −10° C. and tert-butyl 3-formylazetidine-1-carboxylate (2.17 g, 11.7 mmol) dissolved in dry tetrahydrofuran (5 ml) was added in one portion and the temperature was raised to 0° C. and stirred for 20 min and then brought to ambient temperature and stirred for additional 30 min. The reaction mixture was quenched with saturated ammonium chloride solution and extracted with Ethyl acetate. The pooled organic phase was washed with brine, dried (Na2SO4, filtered and evaporated to dryness. The crude product (2.27 g) was further purified by flash column chromatography on silica gel (ethyl acetate: methanol, 50:50) to give the title compound (0.93 g, 3.11 mmol). MS m/z (rel. intensity, 70 eV) 299 (M+, 2), 244 (17), 225 (36), 153(97), 57 (bp)

Preparation 14

Tert-Butyl 3-[(2,4-Difluorophenyl)(Fluoro)Methyl]Azetidine-1-Carboxylate

Tert-butyl 3-[(2,4-difluorophenyl)(hydroxy)methyl]azetidine-1-carboxylate (0.92 g, 3.09 mmol) was dissolved in dry tetrahydrofuran (5 ml) and cooled to 0° C. under nitrogen. Deoxo-fluor (50% in tetrahydrofuran, 1.59 ml, 3.7 mmol) was added in one portion and the mixture stirred for 1 hour and then brought to ambient temperature and stirred for additional 2 hours. The reaction mixture was cooled to 0° C. and water was added dropwise to quench the reaction mixture. The final water solution was extracted with ethyl acetate. The pooled organic phase was washed with brine and dried ($Na_2SO_4$), filtered and finally evaporated to dryness. The crude product was further purified by flash column chromatography on silica gel (iso-octane:ethyl acetate 1:0 to 9:1) to give the title compound (0.54 g, 1.8 mmol). MS m/z (rel. intensity, 70 eV) 301 (M+, 2), 246 (47), 153 (73), 145 (33), 57 (bp)

Preparation 15

Tert-Butyl 3-[(2,6-Difluorophenyl)(Hydroxy)Methyl]Azetidine-1-Carboxylate

To a solution of isopropylmagnesium chloride lithium chloride complex in tetrahydrofuran (1.3 M, 6.3 ml, 8.16 mmol) was added 1-bromo-2,6-difluorobenzene (1.5 g, 7.77 mmol) dissolved in dry tetrahydrofuran (3 ml) and the mixture was stirred under nitrogen at ambient temperature for 1 hour. The reaction mixture was cooled to −10° C. and tert-butyl 3-formylazetidine-1-carboxylate (1.5 g, 8.16 mmol) dissolved in dry tetrahydrofuran (5 ml) was added in one portion and the temperature was raised to 0° C. and stirred for 20 min and then brought to ambient temperature and stirred for additional 30 min. The reaction mixture was quenched with saturated ammonium chloride solution and extracted with Ethyl acetate. The pooled organic phase was washed with brine, dried ($Na_2SO_4$, filtered and evaporated to dryness. The crude product (2.47 g) was further purified by flash column chromatography on silica gel (iso-octane: ethyl acetate 100:0 to 65:35) to give the title compound (2.05 g, 6.85 mmol). MS m/z (rel. intensity, 70 eV) 299 (M+, 2), 225 (37), 154 (21), 153 (bp), 57 (76)

Preparation 16

Tert-Butyl 3-[(2,6-Difluorophenyl)(Fluoro)Methyl]Azetidine-1-Carboxylate

Tert-butyl 3-[(2,6-difluorophenyl)(hydroxy)methyl]azetidine-1-carboxylate (2.0 g, 6.81 mmol) was dissolved in dry methylene chloride (15 ml) and cooled to −78° C. under nitrogen.

Diethylaminosulfur trifluoride (DAST, 1.8 ml, 13.6 mmol) was added in one portion and the mixture stirred for 10 min and then brought to ambient temperature and stirred for additional 1 hour. The reaction mixture was quenched with saturated NaHCO$_3$ aq solution and extracted with methylene chloride. The pooled organic phase was washed with water, brine and dried (Na2SO4), filtered and finally evaporated to dryness. The crude product (1.74 g) was further purified by flash column chromatography on silica gel (iso-octane:ethyl acetate, 100:0 to 85:15) to give the title compound (1.22 g, 4.03 mmol). MS m/z (rel. intensity, 70 eV) 301 (M+, 2), 246 (54), 153 (87), 145 (37), 57 (100)

Preparation 17

Tert-Butyl 3-[Hydroxy(2,3,5-Trifluorophenyl)Methyl]Azetidine-1-Carboxylate

To a solution of isopropylmagnesium chloride lithium chloride complex in tetrahydrofuran (1.3 M, 5.6 ml, 7.3 mmol) was added 1-bromo-2,3,5-trifluorobenzene (1.5 g, 6.97 mmol) dissolved in dry tetrahydrofuran (2 ml) and the mixture was stirred under nitrogen at ambient temperature for 2.5 hours. The reaction mixture was cooled to −10° C. and tert-butyl 3-formylazetidine-1-carboxylate (1.4 g, 7.31 mmol) dissolved in dry tetrahydrofuran (3 ml) was added in one portion and the temperature was raised to 0° C. and stirred for 20 min and then brought to ambient temperature and stirred for additional 30 min. The reaction mixture was quenched with saturated ammonium chloride solution and extracted with ethyl acetate. The pooled organic phase was washed with brine, dried (Na$_2$SO$_4$, filtered and evaporated to dryness. The crude product (2.56 g) was further purified by flash column chromatography on silica gel (iso-octane: ethyl acetate, 100:0 to 80:20) to give the title compound (1.02 g, 3.2 mmol). MS m/z (rel. intensity, 70 eV) 317 (M+, 2), 262 (33), 199 (14), 171 (60), 57 (bp)

Preparation 18

Tert-Butyl 3-[Fluoro(2,3,5-Trifluorophenyl)Methyl]Azetidine-1-Carboxylate

Tert-butyl 3-[hydroxy(2,3,5-triifluorophenyl)methyl]azetidine-1-carboxylate (1.53 g, 4.82 mmol) was dissolved in dry methylene chloride (25 ml) and cooled to −78° C. under nitrogen. Diethylaminosulfur trifluoride (DAST, 1.27 ml, 9.64 mmol) was added in one portion and the mixture stirred for 10 min and then brought to ambient temperature and stirred for additional 1 hour. The reaction mixture was quenched with saturated NaHCO3 aq solution and extracted with methylene chloride. The pooled organic phase was washed with water, brine and dried (Na$_2$SO$_4$), filtered and finally evaporated to dryness. The crude product (1.39 g) was further purified by flash column chromatography on silica gel (iso-octane:ethyl acetate, 100:0 to 85:15) to give the title compound (0.98 g, 3.06 mmol). MS m/z (rel. intensity, 70 eV) 319 (M+, 2), 264 (52), 171 (60), 163 (31), 57 (bp)

Preparation 19

Tert-Butyl 3-[Hydroxy(3,4,5-Trifluorophenyl)Methyl]Azetidine-1-Carboxylate

To a solution of isopropylmagnesium chloride lithium chloride complex in tetrahydrofuran (1.3 M, 5.68 ml, 7.4 mmol) was added 1-bromo-3,4,5-trifluorobenzene (1.5 g, 7.04 mmol) dissolved in dry tetrahydrofuran (3 ml) and the mixture was stirred under nitrogen at ambient temperature for 2.5 hours. The reaction mixture was cooled to −10° C. and tert-butyl 3-formylazetidine-1-carboxylate (1.41 g, 7.4 mmol) dissolved in dry tetrahydrofuran (3 ml) was added in one portion and the temperature was raised to 0° C. and stirred for 20 min and then brought to ambient temperature and stirred for additional 30 min. The reaction mixture was quenched with saturated ammonium chloride solution and extracted with ethyl acetate. The pooled organic phase was washed with brine, dried (Na$_2$SO$_4$, filtered and evaporated to dryness. The crude product (2.41 g) was further purified by flash column chromatography on silica gel (iso-octane: ethyl acetate, 100:0 to 65:35) to give the title compound (1.89 g, 5.95 mmol). MS m/z (rel. intensity, 70 eV) 317 (M+, 2), 262 (29), 171 (52), 145 (16), 57 (bp)

Preparation 20

Tert-Butyl 3-[Fluoro(3,4,5-Trifluorophenyl)Methyl]Azetidine-1-Carboxylate

Tert-butyl 3-[hydroxy(3,4,5-triifluorophenyl)methyl]azetidine-1-carboxylate (1.59 g, 5.01 mmol) was dissolved in dry methylene chloride (15 ml) and cooled to −78° C. under nitrogen. Diethylaminosulfur trifluoride (DAST, 1.32 ml, 10.02 mmol) was added in one portion and the mixture stirred for 10 min and then brought to ambient temperature and stirred for additional 1 hour. The reaction mixture was quenched with saturated NaHCO$_3$ aq solution and extracted with methylene chloride. The pooled organic phase was washed with water, brine and dried (Na2SO4), filtered and finally evaporated to dryness. The crude product (1.6 g) was further purified by flash column chromatography on silica gel (iso-octane:ethyl acetate, 100:0 to 85:15) to give the title compound (1.2 g, 3.77 mmol). MS m/z (rel. intensity, 70 eV) 319 (M+, 1), 264 (33), 171 (34), 163 (21), 57 (bp)

Preparation 21

Tert-Butyl 3-[Hydroxy(2,4,6-Trifluorophenyl)Methyl]Azetidine-1-Carboxylate

To a solution of isopropylmagnesium chloride lithium chloride complex in tetrahydrofuran (1.3 M, 5.74 ml, 7.46 mmol) was added 1-bromo-2,4,6-trifluorobenzene (1.5 g, 7.10 mmol) dissolved in dry tetrahydrofuran (2 ml) and the mixture was stirred under nitrogen at ambient temperature for 3 hours. The reaction mixture was cooled to −10° C. and tert-butyl 3-formylazetidine-1-carboxylate (1.38 g, 7.24 mmol) dissolved in dry tetrahydrofuran (5 ml) was added in one portion and the temperature was raised to 0° C. and stirred for 20 min and then brought to ambient temperature and stirred for additional 30 min. The reaction mixture was quenched with saturated ammonium chloride solution and extracted with ethyl acetate. The pooled organic phase was washed with brine, dried (Na$_2$SO$_4$, filtered and evaporated to dryness. The crude product (1.6 g) was further purified by flash column chromatography on silica gel (iso-octane: ethyl acetate, 100:0 to 75:25) to give the title compound (1.46 g, 4.6 mmol). MS m/z (rel. intensity, 70 eV) 317 (M+, 2), 262 (20), 243 (28), 171 (bp), 57 (90)

Preparation 22

Tert-Butyl 3-[Fluoro(2,4,6-Trifluorophenyl)Methyl]Azetidine-1-Carboxylate

Tert-butyl 3-[hydroxy(2,4,6-triifluorophenyl)methyl]azetidine-1-carboxylate (1.45 g, 4.57 mmol) was dissolved in dry methylene chloride (15 ml) and cooled to −78° C. under nitrogen. Diethylaminosulfur trifluoride (DAST, 1.21 ml, 9.14 mmol) was added in one portion and the mixture stirred for 10 min and then brought to ambient temperature and stirred for additional 1 hour. The reaction mixture was quenched with saturated NaHCO$_3$ aq solution and extracted with methylene chloride. The pooled organic phase was washed with water, brine and dried (Na$_2$SO$_4$), filtered and finally evaporated to dryness. The crude product (1.31 g) was further purified by flash column chromatography on silica gel (iso-octane:ethyl acetate, 100:0 to 85:15) to give the title compound (1.0 g, 3.13 mmol). MS m/z (rel. intensity, 70 eV) 319 (M+, 1), 264 (41), 171 (76), 163 (36), 57 (bp)

Preparation 23

Tert-Butyl 3-[Hydroxy(2,3,4-Trifluorophenyl)Methyl]Azetidine-1-Carboxylate

To a solution of isopropylmagnesium chloride lithium chloride complex in tetrahydrofuran (1.3 M, 5.68 ml, 7.4 mmol) was added 1-bromo-2,3,4-trifluorobenzene (1.5 g, 7.04 mmol) dissolved in dry tetrahydrofuran (3 ml) and the mixture was stirred under nitrogen at ambient temperature for 2.5 hours. The reaction mixture was cooled to −10° C. and tert-butyl 3-formylazetidine-1-carboxylate (1.41 g, 7.4 mmol) dissolved in dry tetrahydrofuran (3 ml) was added in one portion and the temperature was raised to 0° C. and stirred for 20 min and then brought to ambient temperature and stirred for additional 30 min. The reaction mixture was quenched with saturated ammonium chloride solution and extracted with ethyl acetate. The pooled organic phase was washed with brine, dried (Na$_2$SO$_4$, filtered and evaporated to dryness. The crude product was further purified by flash column chromatography on silica gel (iso-octane: ethyl acetate, 100:0 to 70:30) to give the title compound (2.0 g, 6.3 mmol). MS m/z (rel. intensity, 70 eV) 317 (M+, 2), 262 (29), 243 (18), 171 (81), 57 (bp)

Preparation 24

Tert-Butyl 3-[Fluoro(2,3,4-Trifluorophenyl)Methyl]Azetidine-1-Carboxylate

Tert-butyl 3-[hydroxy(2,3,4-triifluorophenyl)methyl]azetidine-1-carboxylate (2.0 g, 6.3 mmol) was dissolved in dry methylene chloride (25 ml) and cooled to −78° C. under nitrogen. Diethylaminosulfur trifluoride (DAST, 1.66 ml, 12.6 mmol) was added in one portion and the mixture stirred for 10 min and then brought to ambient temperature and stirred for additional 1 hour. The reaction mixture was quenched with saturated NaHCO$_3$ aq solution and extracted with methylene chloride. The pooled organic phase was washed with water, brine and dried (Na$_2$SO$_4$), filtered and finally evaporated to dryness. The crude product (1.55 g) was further purified by flash column chromatography on silica gel (iso-octane:ethyl acetate, 100:0 to 85:15) to give the title compound (1.2 g, 3.8 mmol). MS m/z (rel. intensity, 70 eV) 319 (M+, 2), 264 (45), 171 (55), 163 (27), 57 (bp).

Preparation 25

Tert-Butyl 3-[Hydroxy(2,3,5,6-Tetrafluorophenyl)Methyl]Azetidine-1-Carboxylate

1-Bromo-2,3,5,6-tetrafluorobenzene (1.59 ml, 12.71 mmol) was dissolved in dry diethyl ether (30 ml) under a nitrogen atmosphere. Then magnesium (350 mg, 14.41 mmol) and a few granules of I$_2$ were added. 1,2-Dibromoethane (0.011 ml, 0.13 mmol) was added and the final mixture stirred at room temperature for one hour. Tert-butyl 3-formylazetidine-1-carboxylate (2.55 g, 13.34 mmol) dissolved in dry diethyl ether (20 ml) was added dropwise plus 15 ml of dry tetrahydrofuran and the final mixture stirred for one hour at room temperature. The reaction mixture was quenched by adding saturated ammonium chloride solution and extracted with ethyl acetate. The pooled organic phase was washed with brine and dried (Na$_2$SO$_4$), filtered and finally evaporated to dryness. The crude product (4.58 g) was further purified by flash column chromatography on silica gel (iso-octane:ethyl acetate, 100:0 to 70:30) to give the title compound (2.8 g, 8.35 mmol). MS m/z (rel. intensity, 70 eV) 335 (M+, 1), 280 (36), 217 (17), 189 (67), 57 (bp).

Preparation 26

Tert-Butyl 3-[Fluoro(2,3,5,6-Tetrafluorophenyl)Methyl]Azetidine-1-Carboxylate

Tert-butyl 3-[hydroxy(2,3,5,6-tetrafluorophenyl)methyl]azetidine-1-carboxylate (2.79 g, 8.36 mmol) was dissolved in dry methylene chloride (30 ml) and cooled to −78° C. under nitrogen. Diethylaminosulfur trifluoride (DAST, 2.2 ml, 16.6 mmol) was added in one portion and the mixture stirred for 10 min and then brought to ambient temperature and stirred for additional 1 hour. The reaction mixture was quenched with saturated NaHCO$_3$ aq solution and extracted with methylene chloride. The pooled organic phase was washed with water, brine and dried (Na$_2$SO$_4$), filtered and finally evaporated to dryness. The crude product (2.72 g) was further purified by flash column chromatography on silica gel (iso-octane:ethyl acetate, 100:0 to 85:15) to give the title compound (2.28 g, 6.76 mmol). MS m/z (rel. intensity, 70 eV) 337 (M+, 1), 282 (44), 189 (35), 181 (23), 57 (bp).

Preparation 27

Tert-Butyl 3-[Hydroxy(2,3,4,5,6-Pentafluorophenyl)Methyl]Azetidine-1-Carboxylate 1-Bromo-2,3,4,5,6-pentafluorobenzene (1.98 ml, 12.03 mmol) was dissolved in dry diethyl ether (30 ml) under a nitrogen atmosphere. Then magnesium (321 mg, 13.23 mmol) and a few granules of I$_2$ were added. 1,2-Dibromoethane (0.0104 ml, 0.121 mmol) was added and the final mixture stirred at room temperature for one hour. Tert-butyl 3-formylazetidine-1-carboxylate (2.41 g, 12.63 mmol) dissolved in dry diethyl ether (20 ml) was added dropwise and the final mixture stirred for one hour at room temperature. The reaction mixture was quenched by adding saturated ammonium chloride solution and extracted with ethyl acetate. The pooled organic phase was washed with brine and dried (Na$_2$SO$_4$), filtered and finally evaporated to dryness. The crude product (4.12 g) was further purified by flash column chromatography on silica gel (iso-octane:ethyl acetate, 100:0 to 65:35) to give the title compound (3.38 g, 9.58 mmol). MS m/z (rel. intensity, 70 eV) 353 (M+, 1), 298 (33), 235 (14), 207 (65), 57 (bp).

Preparation 28

Tert-Butyl 3-[Fluoro(2,3,4,5,6-Pentafluorophenyl)Methyl]Azetidine-1-Carboxylate

Tert-butyl 3-[hydroxy(2,3,4,5,6-pentafluorophenyl)methyl]azetidine-1-carboxylate (3.38 g, 9.57 mmol) was dissolved in dry methylene chloride (30 ml) and cooled to −78° C. under nitrogen. Diethylaminosulfur trifluoride (DAST, 2.52 ml, 19.14 mmol) was added in one portion and the mixture stirred for 10 min and then brought to ambient temperature and stirred for additional 1 hour. The reaction mixture was quenched with saturated $NaHCO_3$ aq solution and extracted with methylene chloride. The pooled organic phase was washed with water, brine and dried ($Na_2SO_4$), filtered and finally evaporated to dryness. The crude product (3.48 g) was further purified by flash column chromatography on silica gel (iso-octane:Ethyl acetate, 100:0 to 85:15) to give the title compound (3.05 g, 8.58 mmol). MS m/z (rel. intensity, 70 eV) 355 (M+, 1), 300 (37), 207 (33), 199 (24), 57 (bp).

The following tests were used for evaluation of compounds as disclosed herein.

In Vivo Test: Behaviour

Behavioural activity was measured using eight Digiscan activity monitors (RXYZM (16) TAO, Omnitech Electronics, Columbus, Ohio, USA), connected to an Omnitech Digiscan analyzer and an Apple Macintosh computer equipped with a digital interface board (NB DIO-24, National Instruments, USA). Each activity monitor consisted of a quadratic metal frame (W×L=40 cm×40 cm) equipped with photo beam sensors. During measurements of behavioural activity, a rat was put in a transparent acrylic cage (W×L×H, 40×40×30 cm) which in turn was placed in the activity monitor. Each activity monitor was equipped with three rows of infrared photo beam sensors, each row consisting of 16 sensors. Two rows were placed along the front and the side of the floor of the cage, at a 90° angle, and the third row was placed 10 cm above the floor to measure vertical activity. Photo beam sensors were spaced 2.5 cm apart. Each activity monitor was fitted in an identical sound and light attenuating box containing a weak house light and a fan.

The computer software was written using object oriented programming (LabVIEW™, National instruments, Austin, Tex., USA).

Behavioural data from each activity monitor, representing the position (horizontal center of gravity and vertical activity) of the animal at each time, were recorded at a sampling frequency of 25 Hz and collected using a custom written LABView™ application. The data from each recording session were stored and analyzed with respect to distance traveled. Each behavioural recording session lasted 60 min, starting approximately 5 min after the injection of test compound.

Compounds disclosed herein have been tested for effects on spontaneous locomotor activity in non-pre-treated Sprague-Dawley rats (based on accumulated distance traveled 0-60 min post dosing), and with doses up to 33 μmol/kg (s.c.).

There were no significant effects, indicating no major effects of the tested compounds on sensorimotor capability (Table 1)

TABLE 1

Effects of compounds disclosed herein on locomotor activity in drug-naïve rats.

| Example | 11 μmol/kg | 33 μmol/kg |
|---|---|---|
| Example 1 | 61% | 91% |
| Example 2 | 152% | 159%* |
| Example 3 | 68% | 46% |

The animals were placed in the motility meters immediately after drug administration and locomotor activity was recorded for 60 minutes (counts/60 min). Results are presented as percent of control means Statistical significance was assessed using Student's t-test (2 tailed) vs controls.
*denotes p < 0.05, n = 5.

In Vivo Test: Neurochemistry

After the behavioural activity sessions, the rats were decapitated and their brains rapidly taken out and put on an ice-cold petri-dish. The brains were dissected into a right and a left part of which the right part was analyzed for neurochemicals with HPLC and the left part was analyzed for gene expression. The limbic forebrain, the striatum, the frontal cortex, the hippocampus and the remaining hemispheral parts of each rat were dissected and frozen. Each brain part was subsequently analyzed with respect to its content of monoamines and their metabolites.

The monoamine transmitter substances (NA (noradrenaline), DA (dopamine), 5-HT (serotonin)) as well as one corresponding acid, (DOPAC (3,4-dihydroxyphenylacetic acid), were quantified in brain tissue homogenates by HPLC separations and electrochemical detection.

The analytical method is based on two chromatographic separations dedicated for amines or acids. Two chromatographic systems share a common auto injector with a 10-port valve and two sample loops for simultaneous injection on the two systems. Both systems are equipped with a reverse phase column (Luna C18 (2), dp 3 μm, 50*2 mm i.d., Phenomenex) and electrochemical detection is accomplished at two potentials on glassy carbon electrodes (MF-1000, Bioanalytical Systems, Inc.). The column effluent is passed via a T-connection to the detection cell or to a waste outlet. This is accomplished by two solenoid valves, which block either the waste or detector outlet. By preventing the chromatographic front from reaching the detector, better detection conditions are achieved. The aqueous mobile phase (0.4 ml/min) for the acid system contains citric acid 14 mM, sodium citrate 10 mM, Methanol 15% (v/v) and EDTA 0.1 mM. Detection potentials relative to Ag/AgCl reference are 0.45 and 0.60V. The aqueous ion pairing mobile phase (0.5 ml/min) for the amine system contains citric acid 5 mM, sodium citrate 10 mM, Methanol 9% (v/v), MeCN 10.5% v/v), decane sulfonic acid 0.45 mM, and EDTA 0.1 mM. Detection potentials relative to Ag/AgCl reference are 0.45 and 0.65V.

Compounds disclosed herein have been shown to increase the DOPAC levels with a regional preference for the frontal cortex (Table 2).

TABLE 2

Effects on tissue levels of DOPAC in two different brain regions after subcutaneous administration to rats (33 μmol/kg)

| Compound | DOPAC striatum ± SEM | DOPAC frontal cortex ± SEM |
|---|---|---|
| Example 1 | 100 ± 8 | 188 ± 20** |
| Example 3 | 83 ± 2** | 161 ± 6*** |
| Example 6 | 76 ± 3* | 139 ± 10** |

Each compound of Example 1, Example 3 and Example 6, respectively, was administered subcutaneously (s.c.) 65 min before sacrificing the animals. DOPAC results are presented as percent of control means ± SEM (standard error of the mean). Statistical significance was assessed using Student's t-test (2 tailed) vs controls.
*denotes p < 0.05, p < 0.01, *p < 0.001, n = 5.

In Vivo Test: Oral Bioavailability

Experiments are performed 48 hours after implantation of arterial and venous catheters. Test compound is administered orally at 12.5 µmol/kg or intravenously at 5 µmol/kg using the venous catheters, n=3 per group. Arterial blood samples are then taken during six hours at 0, 3, 9, 27, 60, 120, 180, 240, 300 and, 360 minutes after administration of the test compound. The oral bioavailability was calculated as the ratio of the AUC (Area under curve) obtained after oral administration over the AUC obtained after intravenous administration for each rat. The parameter AUC was calculated according to the following:

AUC: the area under the plasma concentration versus time curve from time zero to the last concentration measured (Clast), calculated by the log/linear trapezoidal method.

The levels of test compound are measured by means of liquid chromatography-mass spectrometry (LC-MS) (Hewlett-Packard 1100MSD Series). The LC-MS module includes a quaternary pump system, vacuum degasser, thermostatted autosampler, thermostatted column compartment, diode array detector and API-ES spray chamber. Data handling was performed with a HP ChemStation rev.A.06.03. system. Instrument settings: MSD mode: Selected ion monitoring (SIM) MSD polarity: Positiv Gas temp: 350° C. Drying gas: 13.0 l/min Nebulizer gas: 50 psig Capillary voltage: 5000 V Fragmentor voltage: 70 V Analytical column: ACE EXCEL 3 C18-PFP (3.0*100 mm, 3.0 µm) at 20° C. The mobile phase was acetic acid (0.03%) (solvent A) and acetonitrile (solvent B). The flow rate of the mobile phase was 0.5 ml/min. The elution was starting at 5% of solvent B, then increasing linearity to 70% over 7 min.

Extractions Procedure:

100 µl of plasma samples are mixed with 400 µl ACN containing internal standard. After mixing, the samples are centrifuged 10 min, 4° C., 14000 rpm. The supernatants are transferred to other tubes and evaporated under a stream of nitrogen. The residue was then dissolved in 150 µl 0.1% HAc, centrifuged and transferred to 100 µl glass vials for LC-MS analysis (10 µl injected). The selective ion (MH+) was monitored. A standard curve over the range of 1-500 µmol is prepared by adding appropriate amounts of test compounds to blank plasma samples.

In Vitro Test: Metabolic Stability in Rat Liver Microsomes

Pooled male rat liver microsomes (RLM) (20 mg/ml) was bought from BD Bioscience (#452501). Pooled male dog liver microsomes (DLM) (20 mg/ml) was bought from BD Bioscience (#452601).

Pooled human liver microsomes (HLM) (20 mg/ml) was bought from BD Bioscience (#452161). 1 µL of, 0.2 or 1 mM test substance diluted in water, and 10 µl 20 mg/mL rat liver microsomes were mixed with 149 µl 37° C. buffer 1 and the reaction was started by addition of 40 µL 4.1 mg/mL NADPH. After 15 or 60 minutes incubation at 37° C. in a heating block (LAB-LINE, MULTI-BLOK Heater or lab4you, TS-100 Thermo shaker at 700 rpm) the reaction was stopped by addition of 100 µl pure acetonitrile. The protein precipitation was then removed by rejecting the pellet after centrifugation at 10.000 g for 10 minutes (Heraeus, Biofuge fresco) in 4° C. The test compound was analyzed using HPLC-MS (Hewlett-Packard 1100MSD Series) with a Zorbax SB-C18 column (2.1*150 mm, 5 µm) using 0.03% formic acid and acetonitrile as mobile phase (gradient) or an ACE EXCEL 3 C18-PFP (3.0*100 mm, 3.0 µm) using 0.03% acetic acid and acetonitrile as mobile phase (gradient). The 15 min turnover was calculated as the fraction of test compound eliminated after 15 minutes, expressed in percent of 0 min levels, i.e. 100*[conc. test compound at 0 min−concentration at 15 min]/conc. at 0 min. Protocols for incubation with liver microsomes are referred in Crespi C L and Stresser D M, J Pharm Tox Meth, 2000, 44; 325-31 and Renwick A B et al., Xenobiotica, 2001, 31(4); 187-204.

Microdialysis

Male Sprague-Dawley rats weighing 280-320 g were used throughout the experiments. Before the experiment the animals were housed in groups, maximum five animals in each cage, with free access to water and food. The animals were housed at least one week prior to surgery and use in the experiments.

A modified version (Waters et al., J Neural Transm Gen Sect, 1994, 98(1); 39-55) of the I-shaped probe (Santiago and Westerink, N-S Arch Pharmacol, 1990, 342; 407-14) with the AN69 polyacrylonitrile/sodium methyl sulfonate copolymer (HOSPAL; o.d/i.d. 310/220 µm: dialysis membrane (Gambro, Lund, Sweden) was used in the microdialysis experiments. In the dorsal striatum, probes with an exposed length of 3 mm of dialysis membrane were used and in the prefrontal cortex the corresponding length was 2.5 mm. The rats were operated under isoflurane inhalation anesthesia while mounted into a Kopf stereotaxic instrument. Coordinates were calculated relative to bregma; dorsal striatum AP+1.0, ML±2.6, DV 6.2; Pf cortex, AP 15+3.2, ML+1.2, DV −4.08°, according to Paxinos and Watson (New York, Academic Press, 1986; FIG. 8 and FIG. 14). The dialysis probe was positioned in a burr hole under stereotaxic guidance and cemented with phosphatine dental cement (DAB Dental).

The rats were housed individually in cages for 48 h before the dialysis experiments, allowing them to recover from surgery and minimizing the risk of drug interactions with the anesthetics during the following experiments. During this period the rats had free access to food and water.

On the day of the experiment the rats were connected to a micro-perfusion pump via a swivel and were replaced in the cage where they could move freely within its confinements. The perfusion medium was a Ringer's solution containing (in mmol/l): NaCl; 140, CaCl2; 1.2, KCl; 3.0, MgCl2; 1.0 (Moghaddam and Bunney. Neurochem., 1989, 53; 652-4). The pump was set to a perfusion speed of 2 µl/min and 40 µl sample volume were collected every 20 min.

The rats were perfused for at least 40 min before sampling began. Five fractions of each 20 min were collected and the last three were used for the establishment of the baseline. After collection of baseline fractions, the pharmacological challenge to the dialysis experiment started. Test compounds were administered by injection (s.c.) in a volume of 5 ml/kg, with 0.9% NaCl (saline) as vehicle.

The analytical method were based on two chromatographic separations dedicated for amines or acids. Two chromatographic systems shared a common auto injector with a 10-port valve and two sample loops for simultaneous injection on the two systems.

The acids were separated by reversed phase chromatography while the amines were separated by reversed phase ion pairing chromatography preceded by a reverse phase separation in a column switching configuration. Three separation columns (Luna C18 (2), dp 3 µm, 2 mm i.d., Phenomenex) of different lengths were used. Electrochemical detection was accomplished on glassy carbon electrodes (MF-1000, Bioanalytical Systems, Inc.)

The aqueous mobile phase (0.6 ml/min) for the acid system contained citric acid (40 mM, dipotassium hydrogen phosphate 10 mM, methanol 8-11% (v/v) and EDTA 0.1 mM. Column length was 30 mm and detection potential relative to Ag/AgCl reference was 0.74V.

The aqueous ion pairing mobile phase (0.4 ml/min) for the amine system contained citric acid 5 mM, sodium citrate 10 mM, acetone 9% (v/v), tetrahydrofurane 3% (v/v), dodecane sulphonic acid 0.025 mM, and EDTA 0.1 mM. Column length was 50 mm and the preceding column was 20 mm. Detection potentials relative to Ag/AgCl were 0.45 and 0.65V. The aqueous mobile phase for the coupled reversed phase separation was identical to the ion pairing mobile phase, except that no dodecane sulphonic acid was added.

After the experiment the rats were uncoupled from the perfusion pump, put to death with pentobarbital vet. and decapitated. The rat brains were rapidly taken out and stored in −20° C. for about 30 min before subsequent inspection of probe localization. The Animal Ethics Committee in Gothenburg, Sweden approved the procedures applied in these experiments.

Data analysis: Only results from rats with correctly positioned dialysis probes, as verified by visual examination of brain tissue post mortem, were included in the statistical analyses. Pre-drug baseline values for each analyte and region were calculated by averaging the levels measured in three consecutive fractions collected immediately before administration of test compound. Monoamine dialysate content at each time-point after dosing was then calculated as the percentage of baseline levels. The data from all rats were then averaged, for each time-point. In the tables presented herein, the maximal increases observed after dosing, i.e. the maximal value of the mean percentages of the pre-drug baseline, are shown. The number of rats used for the calculation of mean percentages for each analyte and region are also given in the tables.

Using in vivo brain microdialysis, compounds disclosed herein have been shown to increase the extracellular levels of dopamine and norepinephrine with a regional preference for the frontal cortex (FC) over striatum (Stri). In some cases serotonin is also increased across brain regions (Table 3).

m-RNA Analysis

Animals were killed 60 min after the injection of the drugs by decapitation and the brains were dissected into four different areas: Limbic system (containing nucleus accumbens, most parts of the olfactory tubercle, ventral pallidum), striatum, frontal cortex, hippocampus and the remaining cortex.

Total RNA was prepared by the guanidin isothiocyanate method (Chomczynski P and Sacchi N, Anal Biochem, 1987, 162(1); 156-9). RNA pellets were solved in RNAse-free water and stored at −80° C. The sample concentration was determined spectrophotometrically by a NanoDrop ND1000 (Saveen Werner). A quality indicator number and an integrity number of r-RNA were measured with an Experion (Bio-rad).

A two-step reversed transcription was performed by using a SuperScript III kit (Invitrogen). 1 µg of total RNA was reverse transcribed with 5 µl 2×RT Reaction Mix, 1 µl RT Enzyme Mix, in a total volume adjusted to 10 µl with DEPC-treated water. 1 U of E. coli RNase H was added. c-DNA was diluted 40 times and stored at −20° C.

Three sequences (one gene of interest and two reference genes) were amplified together in a triplex PCR-reaction. For real-time PCR measurements: 5 µl of c-DNA reaction was amplified in a 20 µl reaction mixture containing 10 µl PerfeCta Multiplex qPCR Supermix (Quanta, VWR), 3.5 µl RNAse-free water, 0.15 µM of each primer and 0.1 µM of each probe. Real-time PCR was measured on CFX96 (Bio-rad) using the following settings for all genes: 3 min pre-incubation at 95° C. followed by 40 cycles of denaturation at 95° C. for 15 s, annealing and elongation at 60° C. for 1 minute.

Reference genes are HPRT and cyclophilin.

Compounds disclosed herein have been shown to increase the Arc mRNA levels with a regional preference for the frontal cortex (Table 3).

TABLE 3

Maximum effect compared to baseline values (percent of control ± SEM) at 16.7* and 50 µmol/kg s.c.

| | Compound | | | | | |
|---|---|---|---|---|---|---|
| | NA Stri ± SEM | DA Stri ± SEM | 5-HT Stri ± SEM | NA FC ± SEM | DA FC ± SEM | 5-HT FC ± SEM |
| Example 1* | 150 ± 30$^c$ | 135 ± 19$^d$ | 171 ± 21$^c$ | 688 ± 102$^e$ | 495 ± 58$^e$ | 146 ± 8$^e$ |
| Example 1 | 145$^a$ | 204 ± 90$^b$ | 184$^a$ | 2018 ± 411$^c$ | 1534 ± 205$^c$ | 188 ± 16$^c$ |
| Example 2 | 126 ± 7$^b$ | 149 ± 7$^b$ | 249 ± 5$^b$ | 394 ± 273$^b$ | 580 ± 223$^b$ | 253 ± 92$^b$ |
| Example 3* | 137$^a$ | 116 ± 4$^c$ | 124 ± 6$^c$ | 534 ± 45$^c$ | 444 ± 51$^c$ | 137 ± 16$^c$ |
| Example 4* | 122$^a$ | 116$^a$ | 198$^a$ | 198$^a$ | 226$^a$ | 170$^a$ |
| Example 5 | 480$^a$ | 136 ± 4$^b$ | 435 ± 61$^b$ | 1107 ± 399$^b$ | 330 ± 75$^b$ | 234$^a$ |
| Example 6 | 1375$^a$ | 242$^a$ | 208$^a$ | 2374 ± 1390$^b$ | 1354 ± 567$^b$ | 182 ± 12$^b$ |
| Example 7 | nd** | 130$^a$ | 213$^a$ | 570 ± 6$^b$ | 860 ± 283$^b$ | 404 ± 21$^b$ |
| Example 8 | nd | 133 ± 15$^b$ | 402 ± 12$^b$ | 400 ± 28$^b$ | 549 ± 163$^b$ | 428 ± 118$^b$ |
| Example 9 | 860$^a$ | 127 ± 13$^b$ | 231 ± 106$^b$ | 840 ± 122$^b$ | 1019 ± 397$^b$ | 207 ± 21$^b$ |
| Example 11 | nd | 85 ± 14$^b$ | 366$^a$ | 342$^a$ | 263$^a$ | 236$^a$ |
| Example 12 | nd | 131$^a$ | 359 ± 105$^b$ | 214 ± 28$^b$ | 252 ± 70$^b$ | 322 ± 4$^b$ |
| Example 16 | nd | 139 ± 4$^b$ | 313 ± 23$^b$ | 272 ± 58$^b$ | 229 ± 23$^b$ | 197 ± 124$^b$ |
| Example 19 | nd | 144 ± 10$^c$ | 170 ± 63$^c$ | 354 ± 54$^c$ | 399 ± 30$^c$ | 212 ± 15$^c$ |
| Example 20 | nd | 111$^a$ | 145$^a$ | 264$^a$ | 362$^a$ | 171$^a$ |
| Example 22 | nd | 158$^a$ | nd | 1261 ± 21$^b$ | 654 ± 212$^b$ | 140$^a$ |

$^a$n = 1,
$^b$n = 2,
$^c$n = 3,
$^d$n = 4,
$^e$n = 7;
**nd = no data

TABLE 4

Effects on tissue levels of Arc in two different brain regions after subcutaneous administration to rats (33 µmol/kg)

| Compound | Arc striatum ± SEM | Arc frontal cortex ± SEM |
|---|---|---|
| Example 1 | 133 ± 9* | 169 ± 8** |
| Example 3 | 90 ± 7 | 137 ± 6* |

Compounds of Example 1 and Example 3, respectively, was administered s.c. 65 min before sacrificing the animals. Results are presented as percent of control means ± SEM. Statistical significance was assessed using Student's t-test (2 tailed) vs controls.
*denotes p < 0.05, **p < 0.01, n = 5.

SEQUENCE LISTING

The primer and probe sequences are as follows for measuring of arc:

```
Activity-regulated gene (Arc) (accession
number U19866)
Sense:
                                       (SEQ ID NO: 1)
5'-GGA GTT CAA GAA GGA GTT TC-3'

Antisense
                                       (SEQ ID NO: 2)
5'-CCA CAT ACA GTG TCT GGT A-3'

Probe:
                                       (SEQ ID NO: 3)
CCG CTT ACG CCA GAG GAA CT
Dye: 5'FAM
Quencher: 3'BHQ1
Product size: 149

Hypoxantine phosphoribosyl transferase (HPRT)
(accession number AF001282)
Sense:
                                       (SEQ ID NO: 4)
5'-AGG GAT TTG AAT CAT GTT TG-3'

Antisense
                                       (SEQ ID NO: 5)
5'-CTG CTA GTT CTT TAC TGG C-3'

Probe:
                                       (SEQ ID NO: 6)
TGT AGA TTC AAC TTG CCG CTG TC
Dye: 5'HEX
Quencher: 3'BHQ1
Product size: 121

Cyclophilin A (cyclo) (accession number M19533)
Sense:
                                       (SEQ ID NO: 7)
5'-CTG GAC CAA ACA CAA ATG-3'

Antisense
                                       (SEQ ID NO: 8)
5'-ATG CCT TCT TTC ACC TTC-3'

Probe:
                                       (SEQ ID NO: 9)
TTG CCA TCC AGC CAC TCA GT
Dye: 5'Texas red
Quencher: 3'BHQ2
Product size: 100
```

The primer and probe sequences are as follows for measuring of bdnf, cfos, gad, glud, penk:

```
Brain Derived Neurotrophic Factor (bdnf)
(accession number NM_012513)
Sense:
                                       (SEQ ID NO: 10)
5'-AAA TTA CCT GGA TGC CGC AAA C-3'

Antisense
                                       (SEQ ID NO: 11)
5'-TGT GAC CCA CTC GCT AAT ACT G-3'

Probe:
                                       (SEQ ID NO: 12)
CAC ACA CGC TCA GCT CCC CAC GG
Dye: 5'FAM
Quencher: 3'BHQ1
Product size: 106

Rattus norvegicus proto-oncogen (c-fos)
(accession number DQ089699)
Sense:
                                       (SEQ ID NO: 13)
5'-CAG AGC ATG GGC AGA AGG-3'
(ref N Zoric)

Antisense
                                       (SEQ ID NO: 14)
5'-AGT TGA TCT GTC TCC GCT TGG-3'

Probe:
                                       (SEQ ID NO: 15)
TCT GTC AGC TCC CTC CTC CGA TTC CG
Dye: 5'FAM
Quencher: 3'BHQ1
Product size: 155

Glutamic acid decarboxylase (GAD 67)
(accession number 34445)
Sense:
                                       (SEQ ID NO: 16)
5'-CTG TTT ATG GAG CGT TTG ATC C-3'

Antisense:
                                       (SEQ ID NO: 17)
5'-GAC TGA GAC TGA CCT TTC TAT G-3'

Probe:
                                       (SEQ ID NO: 18)
GAC TGA ATT GGC CCT TTC TAT G
Dye: 5'FAM
Quencher: 3'BHQ1
Product size: 153

Glutamate dehydrogenase (glud) (accession
number NM_012570)
Sense:
                                       (SEQ ID NO: 19)
5'-AGC CTC TCC TTC CCC ATC C-3'

Antisense
                                       (SEQ ID NO: 20)
5'-CGC CTT CAC CTC ATC CAC AC-3'

Probe:
                                       (SEQ ID NO: 21)
AGC ACA GCC AGC ACC GCA CGC
Dye: 5'FAM
Quencher: 3'BHQ1
Product size: 141

Preproenkephalin (penk) (accession number
NM_017139.1)
Sense:
                                       (SEQ ID NO: 22)
5'-CAT GTG CTG CTT GTG CTG T-3'

Antisense
                                       (SEQ ID NO: 23)
5'-CAG TTG GGT TCA CGG GTT T-3'

Probe:
                                       (SEQ ID NO: 24)
TGC CCT CGT GGT CTG GAT AAC TGC
```

-continued

Dye: 5'FAM
Quencher: 3'BHQ1
Product size: 228

Hypoxantine phosphoribosyl transferase (HPRT) (accession number AF001282)
Sense:
(SEQ ID NO: 25)
5'-GGC CAG ACT TTG TTG GAT TTG-3'

Antisense
(SEQ ID NO: 26)
5'-CCG CTG TCT TTT AGG CTT TG-3'

Probe:
(SEQ ID NO: 27)
TTT CCA CTT TCG CTG ATG ACA CAA ACA T
Dye: 5'HEX
Quencher: 3'BHQ1
Product size: 144

Cyclophilin A (cyclo) (accession number M19533)
Sense:
(SEQ ID NO: 28)
5'-GTC TCT TTT CGC CGC TTG CT-3'

Antisense
(SEQ ID NO: 29)
5'-TCT GCT GTC TTT GGA ACT TTG TCT G-3'

Probe:
(SEQ ID NO: 30)
ATG GTC AAC CCC ACC GTG TTC TTC GAC A
Dye: 5'Texas Red
Quencher: 3'BHQ2
Product size: 127

Correct PCR products are confirmed by agarose gel electrophoresis (2%) PCR products are purified with PCR purification kit from Qiagen (Valencia, Calif., USA). All genes are sequenced at MWG, Germany. The amounts of gene of interests are normalized with the two reference genes HPRT and cyclophilin A with the equation delta-delta CT.

---

The invention claimed is:

1. A compound of Formula I:

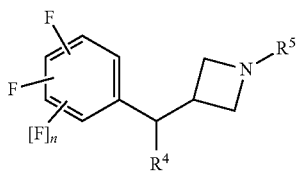

Formula I or a pharmaceutically acceptable salt thereof,
wherein
$R^4$ is F or $CH_3$,
$R^5$ is H or $C_1$-$C_4$alkyl substituted with 0, 1, 2 or 3 F, and
n is 0, 1, 2 or 3.

2. The compound according to claim 1, or a pharmaceutically acceptable salt thereof,
wherein
n is 0 or 1.

3. The compound according to claim 1, or a pharmaceutically acceptable salt thereof, which is a compound of Formula II:

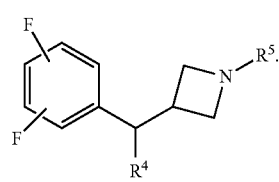

Formula II

4. The compound according to claim 3, or a pharmaceutically acceptable salt thereof, which is selected from the group consisting of a compound of Formula IIa, Formula IIb, Formula IIc, Formula IId, Formula IIe and Formula IIf:

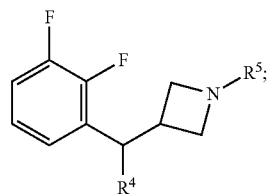

Formula IIa

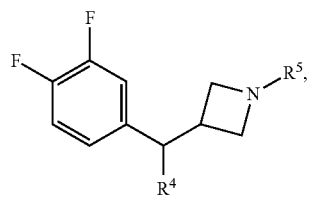

Formula IIb

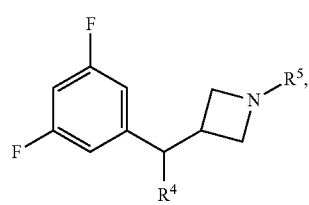

Formula IIc

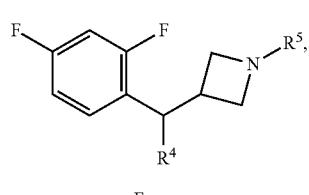

Formula IId

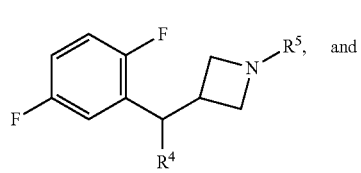

Formula IIe and

Formula IIf

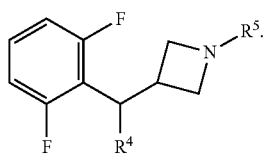

5. The compound according to claim 1, or a pharmaceutically acceptable salt thereof, which is a compound of Formula III:

Formula III

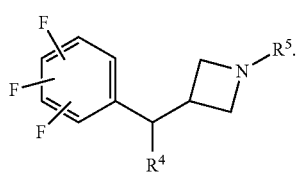

6. The compound according to claim 5, or a pharmaceutically acceptable salt thereof, which is selected from the group consisting of a compound of Formula IIIa, Formula IIIb, Formula IIIc, Formula IIId and Formula IIIe:

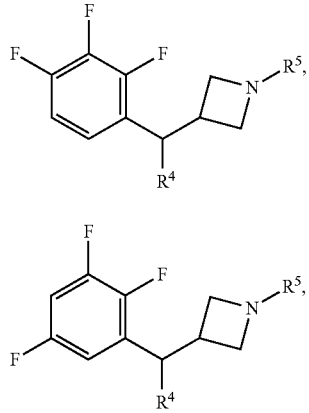

Formula IIIa

Formula IIIb

Formula IIIc

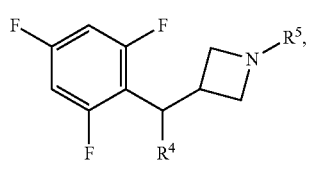

Formula IIId

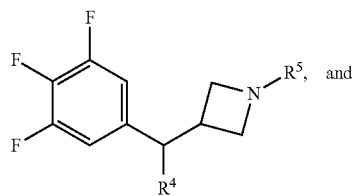

Formula IIIe

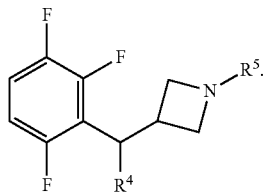

7. The compound according to claim 1, or a pharmaceutically acceptable salt thereof,
wherein
n is 2 or 3.

8. The compound according to claim 7, or a pharmaceutically acceptable salt thereof, which is a compound of Formula IVa, Formula IVb or Formula IVc:

Formula IVa

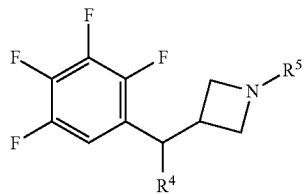

Formula IVb

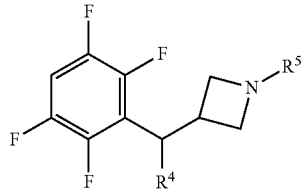

Formula IVc

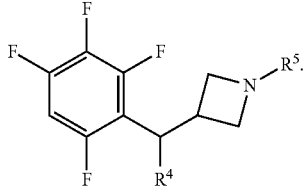

9. The compound according to claim 1, or a pharmaceutically acceptable salt thereof, wherein $R^4$ is F.

10. The compound according to claim 1, or a pharmaceutically acceptable salt thereof, wherein $R^4$ is $CH_3$.

11. The compound according to claim 1, or a pharmaceutically acceptable salt thereof, wherein $R^5$ is H.

12. The compound according to claim 1, or a pharmaceutically acceptable salt thereof, wherein $R^5$ is $C_1$-$C_4$alkyl substituted with 0, 1, 2 or 3 F.

13. The compound according to claim 1, which is:
(−)-3-[(2,3-DIFLUOROPHENYL)(FLUORO)METHYL]AZETIDINE,
(+)-3-[(2,3-DIFLUOROPHENYL)(FLUORO)METHYL]AZETIDINE,
(−)-3-[(3,5-DIFLUOROPHENYL)(FLUORO)METHYL]AZETIDINE,
(+)-3-[(3,5-DIFLUOROPHENYL)(FLUORO)METHYL]AZETIDINE,
3-[(3,4-DIFLUOROPHENYL)(FLUORO)METHYL]AZETIDINE,
3-[(2,5-DIFLUOROPHENYL)(FLUORO)METHYL]AZETIDINE, 3-[(2,6-DIFLUOROPHENYL)(FLUORO)METHYL]
AZETIDINE,
3-[(2,4-DIFLUOROPHENYL)(FLUORO)METHYL]
AZETIDINE,
3-[FLUORO(2,3,5-TRIFLUOROPHENYL)METHYL]
AZETIDINE,
3-[FLUORO(2,4,6-TRIFLUOROPHENYL)METHYL]
AZETIDINE,
3-[FLUORO(2,3,4-TRIFLUOROPHENYL)METHYL]
AZETIDINE,
3-[FLUORO(3,4,5-TRIFLUOROPHENYL)METHYL]
AZETIDINE,
3-[(3,5-DIFLUOROPHENYL)(FLUORO)METHYL]
AZETIDINE,
3-[(2,3-DIFLUOROPHENYL)(FLUORO)METHYL]
AZETIDINE,
3-[(2,3-DIFLUOROPHENYL)(FLUORO)METHYL]-1-
METHYLAZETIDINE,
3-[(2,3-DIFLUOROPHENYL)(FLUORO)METHYL]-1-
ETHYLAZETIDINE,
3-[(2,3-DIFLUOROPHENYL)(FLUORO)METHYL]-1-
PROPYLAZETIDINE,
3-[(3,5-DIFLUOROPHENYL)(FLUORO)METHYL]-1-
METHYLAZETIDINE,
3-[(3,5-DIFLUOROPHENYL)(FLUORO)METHYL]-1-
ETHYLAZETIDINE,
3-[(3,5-DIFLUOROPHENYL)(FLUORO)METHYL]-1-
PROPYLAZETIDINE,
3-[FLUORO(2,3,5-TRIFLUOROPHENYL)METHYL]-
1-METHYLAZETIDINE,
1-ETHYL-3-[FLUORO(2,3,5-TRIFLUOROPHENYL)
METHYL]AZETIDINE,
3-[FLUORO(2,3,5-TRIFLUOROPHENYL)METHYL]-
1-PROPYLAZETIDINE,
1-ETHYL-3-[FLUORO(2,3,4-TRIFLUOROPHENYL)
METHYL]AZETIDINE,
3-[FLUORO(2,3,4-TRIFLUOROPHENYL)METHYL]-
1-PROPYLAZETIDINE,
1-ETHYL-3-[FLUORO(3,4,5-TRIFLUOROPHENYL)
METHYL]AZETIDINE,
3-[FLUORO(3,4,5-TRIFLUOROPHENYL)METHYL]-
1-PROPYLAZETIDINE,
3-[FLUORO(2,3,5,6-TETRAFLUORORPHENYL)
METHYL]AZETIDINE,
3-[FLUORO(PENTAFLUOROPHENYL)METHYL]
AZETIDINE,
3-[FLUORO(2,3,5,6-TETRAFLUOROPHENYL)
METHYL]-1-METHYLAZETIDINE,
1-ETHYL-3-[FLUORO(2,3,5,6-TETRAFLUOROPHE-
NYL)METHYL]-AZETIDINE, or
3-[FLUORO(2,3,5,6-TETRAFLUOROPHENYL)
METHYL]-1-PROPYLAZETIDINE
or a pharmaceutically acceptable salt of any of the foregoing compounds.

14. The compound according to claim 1, which is:
(−)-3-[(2,3-DIFLUOROPHENYL)(FLUORO)
METHYL]AZETIDINE,
(−)-3-[(3,5-DIFLUOROPHENYL)(FLUORO)
METHYL]AZETIDINE, or
(−)-3-[FLUORO(2,3,5-TRIFLUOROPHENYL)
METHYL]AZETIDINE,
or a pharmaceutically acceptable salt of any of the foregoing compounds.

15. The compound according claim 1, or a pharmaceutically acceptable salt thereof, wherein the compound of Formula I is a (−)-enantiomer.

16. The compound according to claim 1 which is a pharmaceutically acceptable salt of the compound of Formula I.

17. A pharmaceutical composition, comprising a therapeutically effective amount of the compound according to claim 1, or a pharmaceutically acceptable salt thereof, together with at least one pharmaceutically acceptable carrier, excipient and/or diluent.

18. A method for treatment of a disease, disorder and/or condition which is responsive to modulation of monoamines in the cerebral cortex which method comprises the step of administering a therapeutically effective amount of a compound of the compound according to claim 1, or a pharmaceutically acceptable salt thereof, to a patient in need thereof,
wherein said disease, disorder and/or condition is selected from the group consisting of dementia, age-related cognitive impairment, cognitive impairment associated with neurodegenerative disorders and/or diseases, autism spectrum disorders, affective disorders, schizophrenia, anxiety disorders, attention deficit hyperactivity disorder (ADHD) and movement disorders.

19. The method according to claim 18, wherein said disease, disorder and/or condition is selected from the group consisting of dementia, age-related cognitive impairment and schizophrenia.

20. The compound according to claim 1, or a pharmaceutically acceptable salt thereof, wherein one or more hydrogen atoms in Formula I are replaced with one or more deuterium atoms.

21. The compound according to claim 1, which is:
(−)-3-[(3,5-DIFLUOROPHENYL)(FLUORO)
METHYL]AZETIDINE,
or a pharmaceutically acceptable salt thereof.

22. The compound according to claim 1, which is:
(−)-3-[FLUORO(2,3,5-TRIFLUOROPHENYL)
METHYL]AZETIDINE,
or a pharmaceutically acceptable salt thereof.

23. The method according to claim 18, wherein the method comprises the step of administering a therapeutically effective amount of a compound of the compound according to claim 21.

24. The method according to claim 23, wherein said disease, disorder and/or condition is selected from the group consisting of dementia, age-related cognitive impairment and schizophrenia.

25. The method according to claim 18, wherein the method comprises the step of administering a therapeutically effective amount of a compound of the compound according to claim 22.

26. The method according to claim 25, wherein said disease, disorder and/or condition is selected from the group consisting of dementia, age-related cognitive impairment and schizophrenia.

* * * * *

UNITED STATES PATENT AND TRADEMARK OFFICE
CERTIFICATE OF CORRECTION

PATENT NO. : 10,087,142 B2  
APPLICATION NO. : 15/574796  
DATED : October 2, 2018  
INVENTOR(S) : Fredrik Pettersson and Clas Sonesson Page 1 of 1

It is certified that error appears in the above-identified patent and that said Letters Patent is hereby corrected as shown below:

In the Claims

Claim 8, Column 72, Line 24 - please insert --,-- after the chemical structure named Formula IVa.

Claim 8, Column 72, Line 31 - please insert --, and-- after the chemical structure named Formula IVb.

Claim 17, Column 74, Line 9 - please remove the "," after the word "composition" and before the word "comprising.".

Signed and Sealed this  
Second Day of July, 2019

Andrei Iancu  
*Director of the United States Patent and Trademark Office*